(12) United States Patent
Hong et al.

(10) Patent No.: US 10,108,833 B2
(45) Date of Patent: Oct. 23, 2018

(54) MARKER FOR OPTICAL TRACKING, OPTICAL TRACKING SYSTEM, AND OPTICAL TRACKING METHOD

(71) Applicant: KOH YOUNG TECHNOLOGY INC., Seoul (KR)

(72) Inventors: Jong Kyu Hong, Anyang-si (KR); Hyun Ki Lee, Daegu (KR)

(73) Assignee: KOH YOUNG TECHNOLOGY INC., Seoul (KR)

( * ) Notice: Subject to any disclaimer, the term of this patent is extended or adjusted under 35 U.S.C. 154(b) by 0 days.

(21) Appl. No.: 15/386,815

(22) Filed: Dec. 21, 2016

(65) Prior Publication Data

US 2018/0046835 A1    Feb. 15, 2018

(30) Foreign Application Priority Data

Aug. 9, 2016  (KR) .................. 10-2016-0101377

(51) Int. Cl.
*G06K 7/14* (2006.01)
*G06K 19/06* (2006.01)
*G06K 7/10* (2006.01)

(52) U.S. Cl.
CPC ....... *G06K 7/1417* (2013.01); *G06K 7/10762* (2013.01); *G06K 7/1443* (2013.01); *G06K 19/06037* (2013.01)

(58) Field of Classification Search
CPC .................................................. G06K 7/1417
USPC ............................ 235/494, 437, 485, 462.25
See application file for complete search history.

(56) References Cited

U.S. PATENT DOCUMENTS

| 4,686,329 | A | 8/1987 | Joyce | |
|---|---|---|---|---|
| 8,880,151 | B1 * | 11/2014 | Stolka | A61B 19/5244 600/424 |
| 2003/0107759 | A1 * | 6/2003 | Athens | G06K 1/121 358/1.15 |
| 2010/0168562 | A1 | 7/2010 | Zhao et al. | |
| 2010/0168763 | A1 | 7/2010 | Zhao et al. | |
| 2011/0017826 | A1 | 1/2011 | Mohan et al. | |

(Continued)

FOREIGN PATENT DOCUMENTS

| JP | 2004-233173 | 8/2004 |
|---|---|---|
| JP | 2006-267879 | 10/2006 |

(Continued)

*Primary Examiner* — Allyson Trail
(74) *Attorney, Agent, or Firm* — Kile Park Reed & Houtteman PLLC

(57) ABSTRACT

The present disclosure provides a marker with a pattern formed thereon, which includes an optical system. At least a part of the pattern that uniquely appears depending on a direction in which the pattern is viewed from an outside of the marker through the optical system, is visually identified from the outside of the marker. The pattern includes a plurality of rows of binary-coded sequences. The binary-coded sequence of each of the plurality of rows includes aperiodic sequences that are repeatedly arranged. The aperiodic sequences included in the binary-coded sequence of one row of the plurality of rows are different from the aperiodic sequences included in the binary-coded sequence of another row of the plurality of rows, and each of the aperiodic sequences includes a plurality of sub-sequences that are arranged in a predetermined order.

32 Claims, 10 Drawing Sheets

(56) References Cited

U.S. PATENT DOCUMENTS

| | | | |
|---|---|---|---|
| 2012/0091204 A1* | 4/2012 | Shi | G06K 7/146 235/437 |
| 2013/0044914 A1* | 2/2013 | Rai | G06K 9/3216 382/103 |
| 2015/0148668 A1 | 5/2015 | Stolka et al. | |
| 2016/0074129 A1* | 3/2016 | Merritt | A61B 90/39 433/29 |
| 2016/0162676 A1* | 6/2016 | Myers | G06F 21/35 726/9 |
| 2016/0171702 A1 | 6/2016 | Wittmeier | |
| 2016/0287341 A1 | 10/2016 | Hong et al. | |
| 2017/0193670 A1 | 7/2017 | Lee et al. | |
| 2017/0200278 A1 | 7/2017 | Lee et al. | |

FOREIGN PATENT DOCUMENTS

| | | |
|---|---|---|
| JP | 2013-205278 | 10/2013 |
| KR | 10-2011-0118639 | 10/2011 |
| KR | 10-2011-0118640 | 10/2011 |
| KR | 10-1406220 | 6/2014 |
| KR | 10-2014-0139698 | 12/2014 |
| WO | 2015/183049 | 12/2015 |
| WO | 2015/183050 | 12/2015 |

* cited by examiner

| One or more capturing elements that are included in one or more capturing units obtain a pattern image for at least a part of a pattern | ⟵ S1210 |

| Processor processes information that is extracted from at least a part of the pattern that is included in the pattern image in order to thereby track the location and the posture of the marker | ⟵ S1220 |

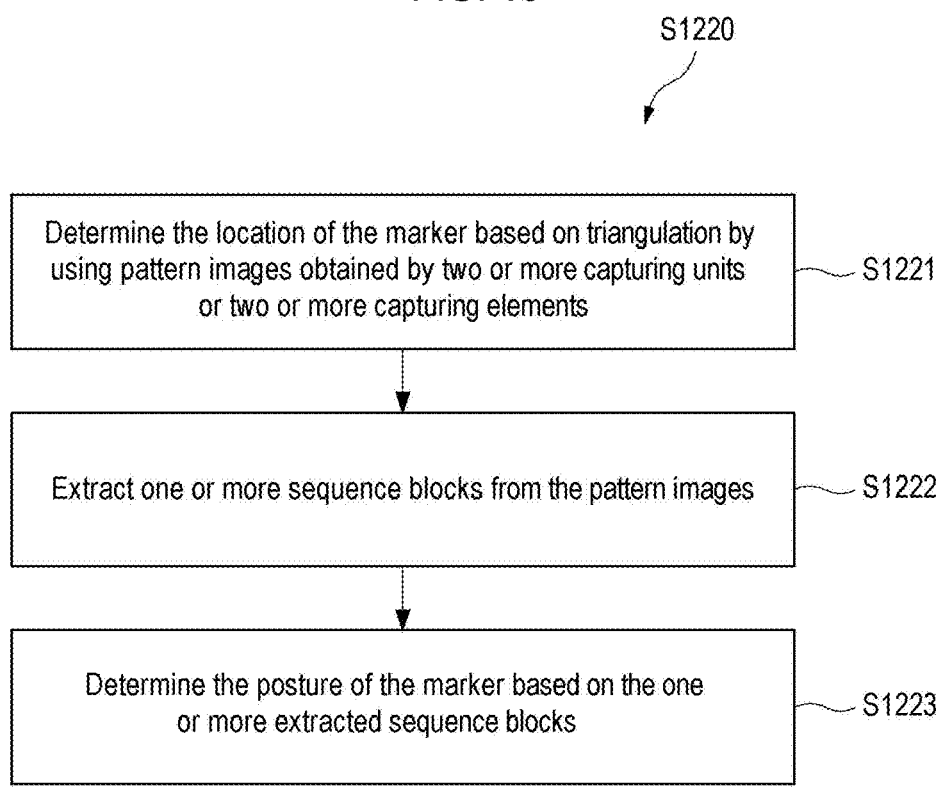

MARKER FOR OPTICAL TRACKING, OPTICAL TRACKING SYSTEM, AND OPTICAL TRACKING METHOD

CROSS-REFERENCE TO RELATED APPLICATIONS

The present application claims priority from Korean Patent Application No. 10-2016-0101377 filed on Aug. 9, 2016, the entire subject matter of which is incorporated herein by reference.

TECHNICAL FIELD

The present disclosure relates to a marker for measuring a location and a posture of a target, and further relates to an optical tracking system and a tracking method using the same.

The present disclosure is derived from research conducted as a part of the Robot Industry Fusion Core Technology Development Project of the Ministry of Trade, Industry and Energy. [Project No. 10062800, Project Title: Development of Practical Technology of Medical Imaging based Brain Surgery Robot System through Clinical Trial]

BACKGROUND ART

An optical tracking system may be used for tracking a target. Recently, in order to process precise surgery while minimizing a risk of the occurrence of surgical errors, a method has been used that tracks the location (or coordinates) and the posture (or orientation) of a surgical robot or a surgical instrument and utilizes the tracking result for surgery. The location of a target, for example, may be defined as spatial coordinates, such as coordinates on the X, Y, and Z axes of an orthogonal coordinate system. The posture of a target may be defined as a roll, pitch, or yaw. In order to accurately track a target, it is important to accurately recognize the location and the posture of the target, which correspond to six degrees of freedom as described above.

In the optical tracking system, for example, after attaching a reference body, such as a marker, to the target, the marker is tracked in order to determine the location and the posture of the target. For example, the location and the posture of a target may be measured by attaching to the target a structure, to which three or more markers are attached. The method of using three or more markers may cause a problem in which it is difficult to reduce the size of the tracking reference body. In particular, when a plurality of markers is attached to a tool, such as a surgical instrument, which is directly navigated by a user, the user may be interrupted or inconvenienced due to its size and weight while using the instrument.

SUMMARY

An aspect of the present disclosure is to provide a marker for optical tracking, which can be lightened and miniaturized.

Another aspect of the present disclosure is to provide an optical tracking system and a method for measuring both the location and the posture of a target by using a light or small marker. For example, the present disclosure provides an optical tracking system and a tracking method for tracking the location and the posture of a target to which one or more markers are attached.

According to one aspect of the present disclosure, a marker with a pattern formed thereon may include an optical system, wherein: at least a part of the pattern that uniquely appears depending on a direction in which the pattern is viewed from an outside of the marker through the optical system, is visually identified from the outside of the marker; the pattern includes a plurality of rows of binary-coded sequences; the binary-coded sequence of each of the plurality of rows includes aperiodic sequences that are repeatedly arranged; the aperiodic sequences included in the binary-coded sequence of one row of the plurality of rows are different from the aperiodic sequences included in the binary-coded sequence of another row of the plurality of rows; and each of the aperiodic sequences includes a plurality of sub-sequences that are arranged in a predetermined order.

According to one embodiment, the plurality of rows of binary-coded sequences may include a first binary-coded sequence and a second binary-coded sequence that are adjacent in a column direction, and a number of bits of each of the sub-sequences included in the first binary-coded sequence is different from a number of bits of each of the sub-sequences included in the second binary-coded sequence.

According to one embodiment, the pattern further include a third binary-coded sequence positioned in a m-th row from the first binary-coded sequence in the column direction and a fourth binary-coded sequence positioned in the m-th row from the second binary-coded sequence in the column direction, wherein the aperiodic sequence included in the third binary-coded sequence may be equal to the aperiodic sequence included in the first binary-coded sequence, and the aperiodic sequence included in the fourth binary-coded sequence may be equal to the aperiodic sequence included in the second binary-coded sequence, and wherein m may be a natural number of 2 or more.

According to one embodiment, the pattern may include: a first sequence group including the first and second binary-coded sequences; a second sequence group including the third and fourth binary-coded sequences; and a meta-sequence configured to separate the first and second sequence groups from each other.

According to one embodiment, the meta-sequence may be different from the binary-coded sequences that are included in the first and second sequence groups.

According to one embodiment, the meta-sequence may be a sequence in which different binary codes are alternately repeated, or may be comprised of only the same binary code.

According to one embodiment, the marker may further include a pattern plane on which the pattern is formed, and different binary codes that are included in the binary-coded sequences of the pattern formed on the pattern plane are made of materials that have different reflectivities from each other.

According to one embodiment, the marker may further include a pattern plane on which the pattern is formed, and the optical system may include a lens, wherein the pattern is formed in a portion where a focal point of the lens is formed on the pattern plane.

According to one embodiment, the pattern plane may have a flat or curved surface, and the lens may allow the focal point to be formed on the flat or curved surface.

According to one embodiment, the aperiodic sequence may be a PRBS (Pseudo-Random Binary Sequence) or De Bruijn Sequence.

According to one embodiment, if at least a part of the pattern is captured as a pattern image in the outside of the marker, a size of a region where at least a part of the pattern is captured on the pattern image varies with at least one of a distance from a location in which the pattern image is captured to the marker or a location of the marker.

According to another aspect of the present disclosure, an optical tracking system may include: one or more markers on which a pattern is formed; one or more capturing units that is configured to include one or more capturing elements that obtains a pattern image of the pattern; and a processor configured to track locations and postures of the one or more markers based on information that is extracted from at least a part of the pattern included in the pattern image, wherein: the pattern includes a plurality of rows of binary-coded sequences; the binary-coded sequence of each of the plurality of rows includes aperiodic sequences that are repeatedly arranged; the aperiodic sequences included in the binary-coded sequence of one row of the plurality of rows are different from the aperiodic sequences included in the binary-coded sequence of another row of the plurality of rows; and each of the aperiodic sequences includes a plurality of sub-sequences that are arranged in a predetermined order.

According to one embodiment, the optical tracking system extracts one or more sequence blocks from the pattern image and then tracks the one or more markers, and wherein the one or more sequence blocks include a part of the plurality of rows of binary-coded sequences.

According to one embodiment, the one or more sequence blocks have a size of j×l in which j denotes a number of binary-coded sequences that are included in the one or more sequence blocks and l denotes a number of bits of a longest sub-sequence among the plurality of sub-sequences included in the one or more sequence blocks.

According to one embodiment, the processor determines postures or IDs of the one or more markers based on the one or more sequence blocks.

According to one embodiment, the part of the plurality of rows of binary-coded sequences are sub-sequences that are included in each of the plurality of rows of binary-coded sequences, and the processor determines a location of a sub-pattern represented by the one or more sequence blocks in the pattern based on the sub-sequences, and determines the postures of the one or more markers based on the location of the sub-pattern.

According to one embodiment, the part of the plurality of rows of binary-coded sequences are sub-sequences that are included in each of the plurality of rows of binary-coded sequences, and the processor determines location information on the one or more sequence blocks in the plurality of binary-coded sequences based on the sub-sequences, and determines the IDs of the one or more markers based on the location information.

According to one embodiment, the one or more capturing units may include two or more capturing units, or the one or more capturing elements may include two or more capturing elements. In addition, the processor determines the locations of the one or more markers based on triangulation by using pattern images that are obtained by the two or more capturing units or by the two or more capturing elements.

According to one embodiment, the processor determines the locations of the one or more markers based on central coordinates of a region of the pattern on each of the pattern images and triangulation by using a geometric relationship between directions in which the two or more capturing units or the two or more capturing elements view the one or more markers.

According to one embodiment, the processor determines the locations of the one or more markers based on a size of a region of the pattern and central coordinates of the pattern region, on the pattern image obtained by the capturing units.

According to one embodiment, the one or more markers may include two markers that have a predetermined geometric relationship, and the capturing units capture pattern images of patterns that are formed on the two markers, respectively. In addition, the processor determines the locations of the two markers based on the predetermined geometric relationship and a relationship between a location of at least a part of the patterns on the pattern images and a location of at least a part of the pattern on each of the markers.

According to one embodiment, the plurality of rows of binary-coded sequences include a first binary-coded sequence and a second binary-coded sequence that are adjacent in a column direction, and a number of bits of each sub-sequence included in the first binary-coded sequence is different from a number of bits of each sub-sequence included in the second binary-coded sequence.

According to one embodiment, the pattern further includes a third binary-coded sequence positioned in a m-th row from the first binary-coded sequence in the column direction and a fourth binary-coded sequence positioned in the m-th row from the second binary-coded sequence in the column direction, wherein the aperiodic sequence included in the third binary-coded sequence may be equal to the aperiodic sequence included in the first binary-coded sequence and the aperiodic sequence included in the fourth binary-coded sequence may be equal to the aperiodic sequence included in the second binary-coded sequence, and wherein m is a natural number of 2 or more.

According to one embodiment, the one or more markers include a first lens, and the pattern is implemented on a pattern plane on which a focal point of the first lens is formed. In addition, the one or more capturing units include a second lens that is configured such that at least a part of the pattern, which is visually identified from the one or more markers in a direction in which the capturing units view the one or more markers through the first lens, is captured on the one or more capturing elements, and obtains a pattern image of at least a part of the pattern in a focal length of the second lens.

According to one embodiment, the optical tracking system may further include a light source configured to emit light onto the one or more markers in order to enhance the light incident on the second lens through the first lens with respect to at least a part of the pattern.

According to still another aspect embodiment of the present disclosure, an optical tracking method for tracking a marker on which a pattern is formed is disclosed. The method may include: obtaining, by one or more capturing elements included in one or more capturing units, a pattern image of at least a part of the pattern; and proceeding, by a processor, information extracted from at least a part of the pattern included in the pattern image and tracking a location and a posture of the marker, wherein: the pattern includes a plurality of rows of binary-coded sequences; the binary-coded sequence of each of the plurality of rows includes aperiodic sequences that are repeatedly arranged; the aperiodic sequences included in the binary-coded sequence of one row of the plurality of rows are different from the aperiodic sequences included in the binary-coded sequence of another row of the plurality of rows; and each of the aperiodic sequences includes a plurality of sub-sequences that are arranged in a predetermined order.

According to one embodiment, the tracking the location and the posture of the marker includes extracting one or more sequence blocks from the pattern image, and the one or more sequence blocks have a size of j×1 in which j denotes a number of binary-coded sequences that are included in the one or more sequence blocks and 1 denotes a number of bits of a longest sub-sequence among the sub-sequences included in the one or more sequence blocks.

According to one embodiment, the tracking the location and the posture of the marker includes determining the posture of the marker based on the one or more extracted sequence blocks.

According to one embodiment, the determining the posture of the marker includes: determining a location of a sub-pattern represented by the one or more sequence blocks in the pattern based on the sub-sequences that are included in each of the plurality of rows of binary-coded sequences that are included in the one or more sequence blocks; and determining the posture of the marker based on the determined location of the sub-pattern.

According to one embodiment, the one or more capturing units may include two or more capturing units, or the one or more capturing elements may include two or more capturing elements. In addition, the tracking the location and the posture of the marker comprises determining the location of the marker based on triangulation by using pattern images that are obtained by the two or more capturing units or by the two or more capturing elements.

According to one embodiment, the determining the location of the marker based on the triangulation includes determining the location of the marker based on central coordinates of the pattern region on each of the pattern images and triangulation by using a geometric relationship between directions in which the two or more capturing units or the two or more capturing elements view the marker.

A computer-readable recording medium according to an exemplary embodiment of the present disclosure may store a program that may execute operations of the optical tracking method according to an exemplary embodiment of the present disclosure.

The marker, according to one embodiment of the present disclosure, may be implemented to be small.

In addition, according to the optical tracking system by using a marker in accordance with one embodiment of the present disclosure, it is possible to measure, by using one or more markers, the location and the posture of a target having the attached markers, which correspond to six degrees of freedom.

Furthermore, according to the optical tracking system by using a marker in accordance with one embodiment of the present disclosure, the distance in which the tracking can be made may increase, and it is possible to reduce a tracking error that occurs because a part of the pattern included in the marker is obscured.

BRIEF DESCRIPTION OF THE DRAWINGS

Embodiments of the inventive aspects of this disclosure will be understood with reference to the following detailed description, when read in conjunction with the accompanying drawings.

FIG. 13 is a flowchart of a method for tracking the location and the posturea location and a posture of a marker in an optical tracking system, according to one embodiment of the present disclosure.

DETAILED DESCRIPTION

Figure 1:
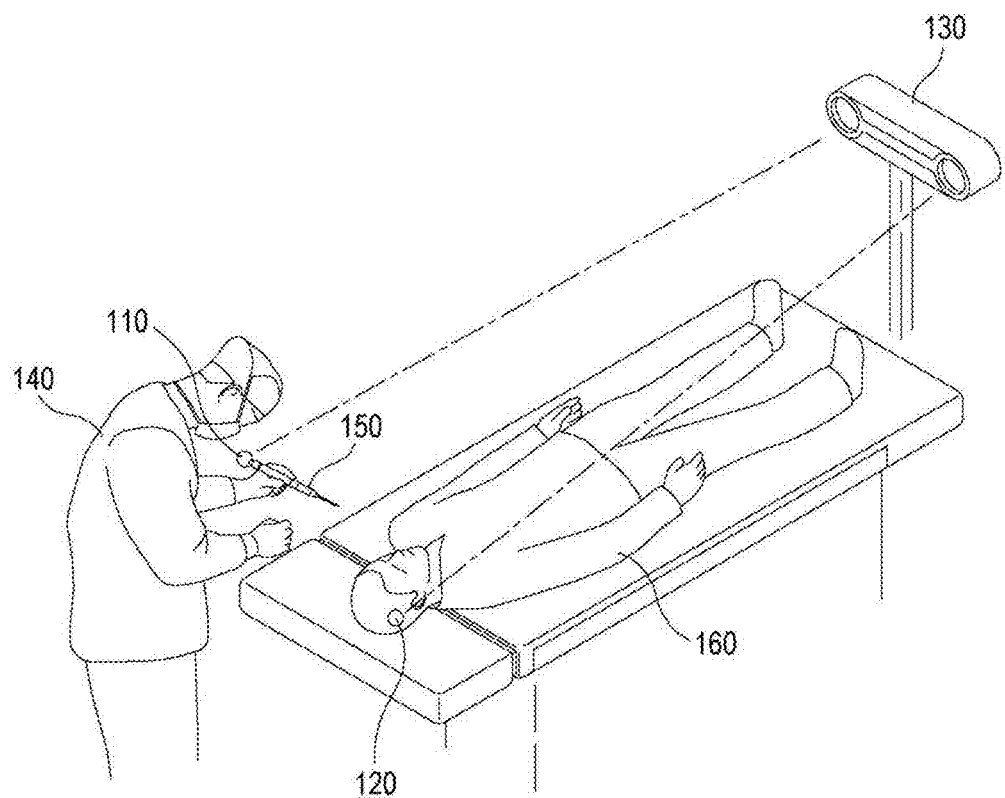
FIG. 1 describes an optical tracking system used for surgery, according to one embodiment of the present disclosure.

Embodiments of the present disclosure are only examples that are illustrated for the purpose of explaining the present disclosure. The embodiments of the present disclosure may be conducted in various manners, and the present disclosure shall not be construed to be limited to the embodiments described below or to the detailed description of the embodiments.

The term "unit" used in the present embodiments refers to a software element or a hardware element, such as FPGA (field-programmable gate array), ASIC (application specific integrated circuit), etc. However, the "unit" is not limited to hardware and software. The "unit" may be configured to be in a storage medium that can be addressed, and may be configured to reproduce one or more processors. Accordingly, as an example, the "unit" includes elements, such as software elements, object-oriented software elements, class elements, task elements, etc., processors, functions, attributes, procedures, subroutines, program code segments, drivers, firmware, micro-codes, circuits, data, databases, data structures, tables, arrays, and variables. Functions that are provided in the elements and "unit" may be combined into fewer elements and "units," or may be further divided into additional elements and "units."

All the technical terms and scientific terms in the present specification include meanings or definitions that are commonly understood by those of ordinary skill in the art unless otherwise defined. All terms in the present specification are selected for the purpose of describing the present disclosure more clearly, and are not selected to limit the scope of the present disclosure.

The singular expressions that are described in the present specification may encompass plural expressions unless otherwise stated, which will be also applied to the singular expressions recited in the claims.

The expressions, such as "first," "second," etc., which are shown in various embodiments of the present disclosure, are used to separate a plurality of elements from each other, and are not intended to limit an order or importance of the corresponding elements.

The expressions, such as "include" or "have," which are used in the present specification, should be appreciated as open-ended terms that include a possibility of including other embodiments unless particularly otherwise stated in the phrase or sentence that contains the corresponding expressions.

In the present specification, the expression "based on" will be used to describe one or more factors that affect an act or operation of a decision or determination that is described in the phrase that contains the corresponding expression, and does not exclude additional factors that affect the act or operation of the decision or determination.

In the present specification, the description that one element is "connected," or "coupled" to another element should be appreciated to indicate that one element may be directly connected, or coupled, to another element, and should be further understood that a new element may be interposed between one element and another element.

Hereinafter, the embodiments of the present disclosure will be described in detail with reference to the accompanying drawings. The same reference numeral will be used for the same element throughout the drawings, and a duplicate description of the same element will be omitted.

<Optical Tracking System>

FIG. 1 describes an optical tracking system used for surgery, according to one embodiment of the present disclosure. As shown, a surgeon 140 may proceed with surgery for a patient 160 by using a surgical instrument 150 and the optical tracking system, which includes a capturing unit 130. A marker 110 may be attached to the surgical instrument 150 that is used by the surgeon 140, and another marker 120 may be attached to a target, such as an affected portion of the patient 160. The capturing unit 130 of the optical tracking system may capture and obtain a pattern image for the whole pattern or a part of a pattern formed on the marker 110 or 120. The pattern image may be captured in a partial region in a frame of a captured image that is output by an image sensor of the capturing unit 130.

When the pattern image is obtained, one or more sub-patterns may be extracted from the pattern image as a basic unit constituting the pattern of the marker. According to some embodiments, locations of the one or more extracted sub-patterns in the entire pattern may be determined, and the posture of the marker 110 or 120 may be determined based on the determined the locations of the sub-patterns in the entire pattern. In this case, the posture of the marker 110 or 120 may be referred to a relative three-dimensional direction or orientation of the marker 110 or 120 with respect to the capturing unit 130.

In addition, according to one embodiment, a location of one of the markers 110 and 120 in a three-dimensional space may be determined based on a size and coordinates of at least one pattern image in a captured image that is captured by one or more capturing units 130 that include one or more capturing elements.

In some embodiments, the capturing unit 130 may include two or more cameras, and a location of one of the markers 110 and 120 may be determined by using triangulation based on the pattern images captured by the cameras.

According to one embodiment, two markers 110 and 120 that have a predetermined geometric relationship may be attached to a single target. In this case, the locations of the markers 110 and 120 in the three-dimensional space may be determined based on the predetermined geometric relationship of the markers 110 and 120 and a relationship between a location of at least a part of the pattern on the pattern image and a location of at least a part of the pattern (e.g., a corresponding part) on each of the markers 110 an 120.

When the location and the posture of the marker 110 or 120 are obtained as described above, the location and the posture of a target to which the marker 110 or 120 is attached may be determined based on a geometric relationship between the marker 110 or 120 and the target to which the marker 110 or 120 is attached.

According to some embodiments, one embodiment the location and the posture of the target corresponding to six degrees of freedom may be determined by using one or more markers in the optical tracking system, which will be described in detail below.

Figure 2:
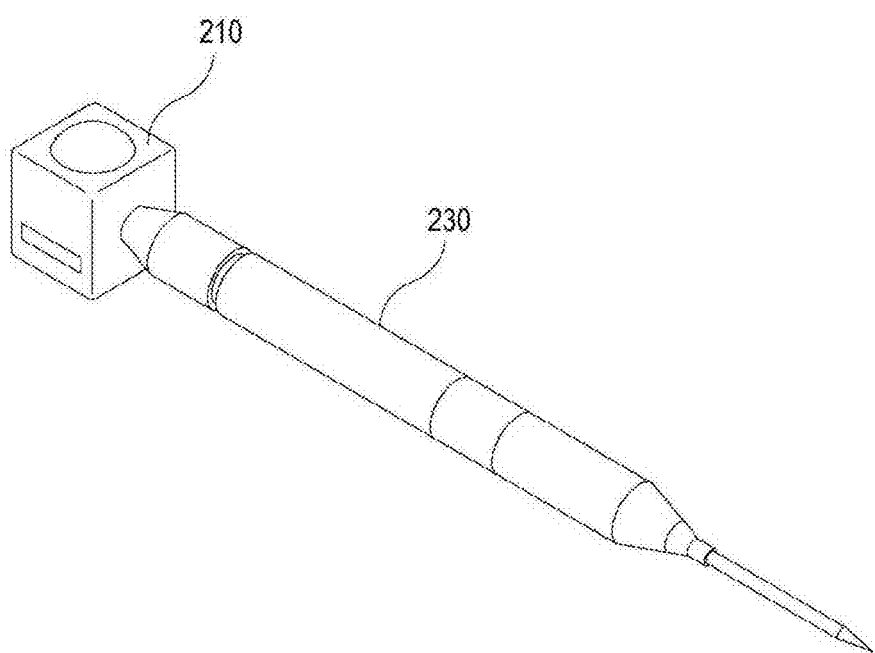
FIG. 2 is a surgical instrument where a marker is attached and used, according to one embodiment of the present disclosure.

FIG. 2 depicts a surgical instrument 230 to which a marker 210 is attached, according to one embodiment of the present disclosure. In one embodiment of the optical tracking system of the present disclosure, even in the case where a single marker 210 is attached to the surgical instrument 230 as a target, the location and the posture of the target may be tracked based on a pattern formed on the marker 210. Therefore, a light or small marker may be attached to the surgical instrument 230, and a surgeon may proceed with surgery by using the surgical instrument 230 with the marker attached without concerning about a size or weight of the marker.

In one embodiment, the marker may be attached to or detached from a target to be tracked. As shown in FIG. 2, when preparing for a surgery process, the marker 210 may be sterilized before it is attached to the surgical instrument 230. In this case, since only a single marker 210 needs to be attached to the surgical instrument 230, the attachment/detachment process may be simplified. In addition, since only a single marker 210 needs to be sterilized, it is possible to reduce the time and the effort required for the surgery preparation including a disinfection process. As the number of targets to which the marker is attached for surgery increases, the number of markers to be attached or detached may increase. Thus, in the case of using a single marker, it is possible to reduce time and cost for the surgery preparation.

Although the marker and the optical tracking system, according to the present disclosure, are used in a surgery of a patient by a surgeon in the embodiments described above, they may also be used in various other instances for determining the location and the posture of a target by using a marker. For example, the marker and the optical tracking system, according to the present disclosure, may be used for determining the location and the posture of a surgical instrument that is attached to a surgical robot when a patient undergoes surgery using the surgical robot. In another example, the marker and the optical tracking system, according to the present disclosure, may be used for determining the location and the posture of a specific instrument and/or target when a specific operation is performed with respect to the target using the instrument by an operator or surgical robot. The various embodiments of the marker and the optical tracking system of the present disclosure, which have been described through the examples of FIGS. 1 and 2, will be described in more detail below.

Figure 3:
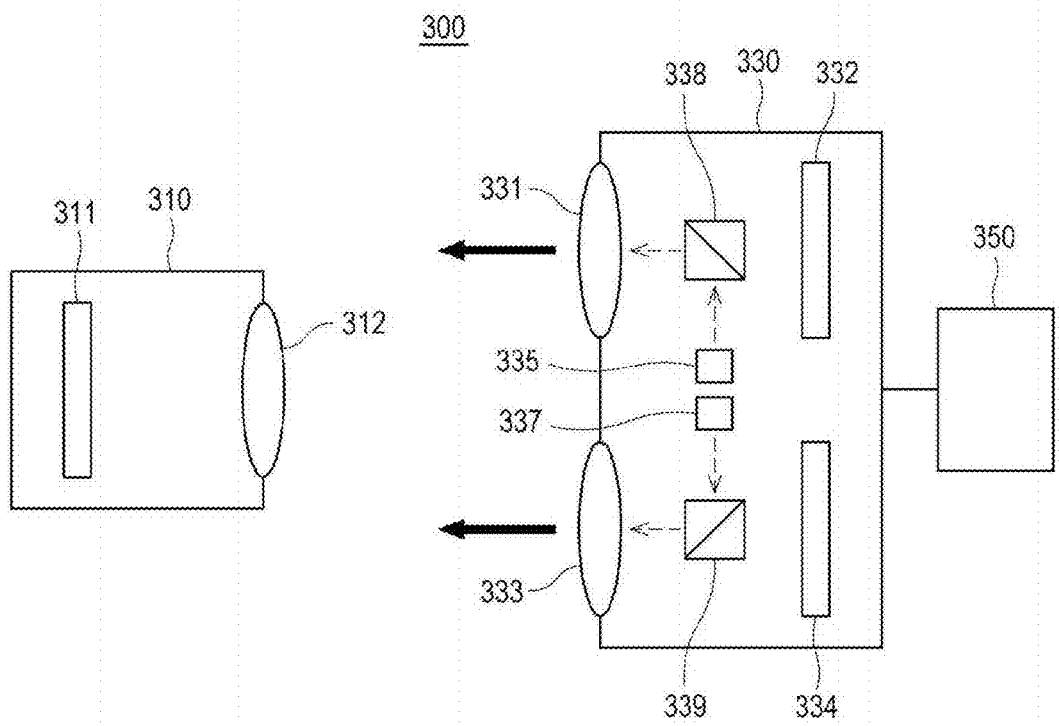
FIG. 3 depicts a block diagram of an optical tracking system including a marker, according to one embodiment of the present disclosure.

FIG. 3 depicts a block diagram of an optical tracking system 300, according to one embodiment of the present disclosure. The optical tracking system 300 may include a marker 310, a capturing unit 330, and a processor 350. The marker 310 may include a pattern plane 311 on which a pattern is formed and an optical system 312, such as lenses, that is configured to allow at least a part of the pattern, which uniquely appears according to a viewing direction from the outside of the marker, to be identified (or visually recognized) from the outside of the marker 310. In one embodiment, when the marker 310 belongs to the field of view (FOV) of the capturing unit 330 and the optical system 312 is arranged toward the capturing unit 330, the capturing unit 330 may capture at least a part of the pattern that is identified through the optical system 312.

The capturing unit 330 may include lenses and capturing elements that can capture and obtain a pattern image including at least a part of the pattern. Any type of capturing element may be provided, which is configured to obtain a captured image for any object, and the capturing element, for example, may include a CCD (charge-coupled device), CMOS (complementary metal-oxide semiconductor) image sensor, or the like.

According to one embodiment, the capturing unit 330 may include a plurality of capturing elements 332 and 334. The capturing elements 332 and 334 may obtain pattern images of the marker 310 identified through the respective lenses 331 and 333. The capturing elements 332 and 334 may be disposed at an angle to obtain a pattern image including at least a part (or the same region) of the pattern that is formed on the marker 310. Even though the number of the capturing elements is 2 (two) in FIG. 3, the capturing unit 330 may include three or more of capturing elements.

According to some embodiments, the optical tracking system 300 may further include one or more light sources for emitting the light onto the marker 310 or the pattern in order to enhance the light incident on the lenses 331 and 333 through the optical system 312 so that the pattern can be properly identified from the outside of the marker 310.

In one embodiment, the light source may be installed in the outside of the marker 310. In this case, the marker 310 may operate as a passive marker. If the marker 310 operates as a passive marker, the capturing unit 330 may include one or more light sources 335 and 337 to emit the light onto the marker 310. As shown in FIG. 3, the light from the light source 335 may be reflected by a beam splitter 338 and be then emitted onto the marker 310 through the lens 331. The light from the other light source 337 may be reflected by a beam splitter 339 and be then emitted onto the marker 310 through the lens 333. In this configuration, the light that is reflected by the beam splitter 338 or 339 and is then emitted onto the marker 310 through the lens 331 or 333 from the capturing unit 330 and the light that is reflected by the pattern of the marker 310 and is then received through the lens 331 or 333 of the capturing unit 330 may travel through the same path with respect to the lenses 331 and 333. In this case, since the amount of the light that is reflected by the marker 310 and is then received by the capturing unit 330 may increase, the capturing elements 332 and 334 may capture even clearer pattern images.

According to another embodiment, the light source may be installed to emit the light to the front or back surface of the pattern plane 311 inside the marker 310. In this case, the marker 310 may operate as an active marker. In addition, the light sources 335 and 337 and the beam splitters 338 and 339, which are installed in the capturing unit 330 as shown in FIG. 3, may be omitted.

The processor 350 may be configured to receive the pattern image obtained in the capturing unit 330, and may determine the location and the posture of the marker 310 based on the received pattern image. In one embodiment, the processor 350 may determine the location of the marker 310 based on the size of at least a part (or region) of the pattern contained in the pattern image and the central coordinates of the region, or may determine the location of the marker 310 by using triangulation. In addition, the processor 350 may determine a location of each of the sub-patterns, which constitute the pattern, in the entire pattern based on the pattern image, and may determine the posture of the marker 310 based on the locations of the sub-patterns. The method for determining the location and the posture of the marker 310 will be described in more detail below.

In one embodiment, if the optical tracking system 300 operates in a surgical system, such as a surgical navigation system, the marker 310 may be attached to one or more targets that include a surgical instrument, a part of a surgical robot, or an affected portion of a patient. In addition, in the case of using a plurality of markers, the locations and postures of the markers may be tracked at the same time or sequentially. In this case, the processor 350 may distinguish the markers attached to the respective targets based on IDs of the markers in order to track the locations and postures of the markers. According to one embodiment, the processor 350 may extract an ID of the marker 310 from the pattern image. The method for extracting and obtaining an ID of the marker 310 will be described in more detail later.

Figure 4:
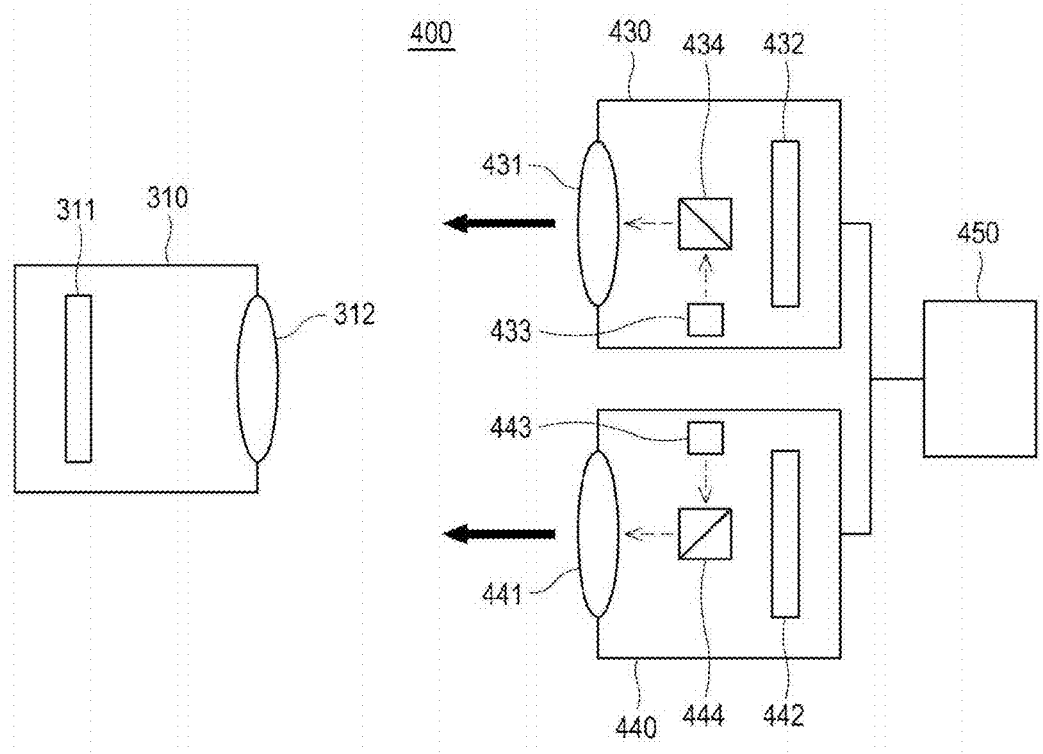
FIG. 4 illustrates a block diagram of an optical tracking system including a marker, according to another embodiment of the present disclosure.

According to another embodiment, as shown in FIG. 4, the optical tracking system 400 may include a plurality of capturing units 430 and 440. The directions or angles of the capturing units 430 and 440 toward the marker may be configured such that the respective capturing units 430 and 440 can obtain pattern images for the same region of the pattern formed on the marker 310. Even though the number of the capturing elements is 2 (two) in FIG. 4, the capturing unit 330 may include three or more of capturing elements.

According to one embodiment, when the marker 310 operates as a passive marker, the capturing units 430 and 440 may include light sources 433 and 443, respectively, which can emit the light onto the marker 310. In this case, the light emitted from the light source 433 may be reflected by a beam splitter 434 and be then transferred to the marker 310 through a lens 431. In addition, the light emitted from another light source 443 may be reflected by a beam splitter 444 and be then transferred to the marker 310 through a lens 441.

The processor 450 may determine the location and the posture of the marker 310 based on the information extracted from at least a part of the pattern, which is included in the pattern image obtained by the capturing elements 432 and 442 in the respective capturing units 430 and 440. A method for determining the location and the posture of the marker 310 by using a pattern image is executed in the same manner as the method described above, which will be also described in more detail below.

According to another embodiment, the optical tracking system may track locations and postures of two markers having a predetermined geometric relationship between them. The optical tracking system may obtain pattern images of patterns formed on two markers, respectively, through a single capturing element. The locations of two markers may be determined based on the predetermined geometric relationship and a relationship between the location of at least a part of the pattern on the pattern image and the location of at least the corresponding part of the pattern on each of markers. The posture of the marker may be determined in the same manner as that described above.

<Marker>

The marker 310 may be attached to a target of which the location and the posture are measured by the optical tracking system 300 or 400, or may be implemented by the whole or a part of the target. The location and the posture of the target to which the marker 310 is attached may be measured by measuring the location and the posture of the marker 310. In one embodiment, the marker 310 may include the pattern plane 311 and the optical system 312, such as lenses, as described with reference to FIGS. 3 and 4 above.

According to some embodiments, the marker 310 may be implemented by using a material, such as resin, aluminum, or the like, which is a light material and is not damaged by medical substances, such as a disinfectant. When the marker 310 is attached to an instrument or device used for surgery, the marker 310 may be sterilized before it is used in the surgery. In this case, the marker 310 is required to be implemented by using a material that is not damaged by the disinfectant.

The marker 310 may have an outer shape to allow the pattern plane 311 and the optical system 312, such as lenses, to be easily installed. According to one embodiment, the marker 310 may have a cylindrical shape. If the marker 310 has a cylindrical shape, the optical system 312 may be installed on one side of the cylindrical shape, and the pattern plane 311 may be installed on the other side that faces the one side on which the optical system 312 is installed. In this configuration, a pattern formed on the pattern plane 311 may be visually identified through the body of the cylinder and then through the optical system 312 from the outside. According to another embodiment, the marker 310 may have a spherical or cubic shape. If the marker 310 has a spherical shape, the pattern plane 311 on which the pattern is formed may be implemented in at least a portion of the inner surface or outer surface of the sphere, and the optical system 312 may be implemented in another portion that faces the pattern plane 311 on the inner surface of the sphere.

Since the pattern is formed such that the location of each of the sub-patterns is uniquely determined throughout the entire pattern, the information on the location of each sub-pattern in the entire pattern may be extracted from the pattern image of the pattern. In addition, the pattern may be formed so as to provide the ID of the marker 310.

Figure 5:
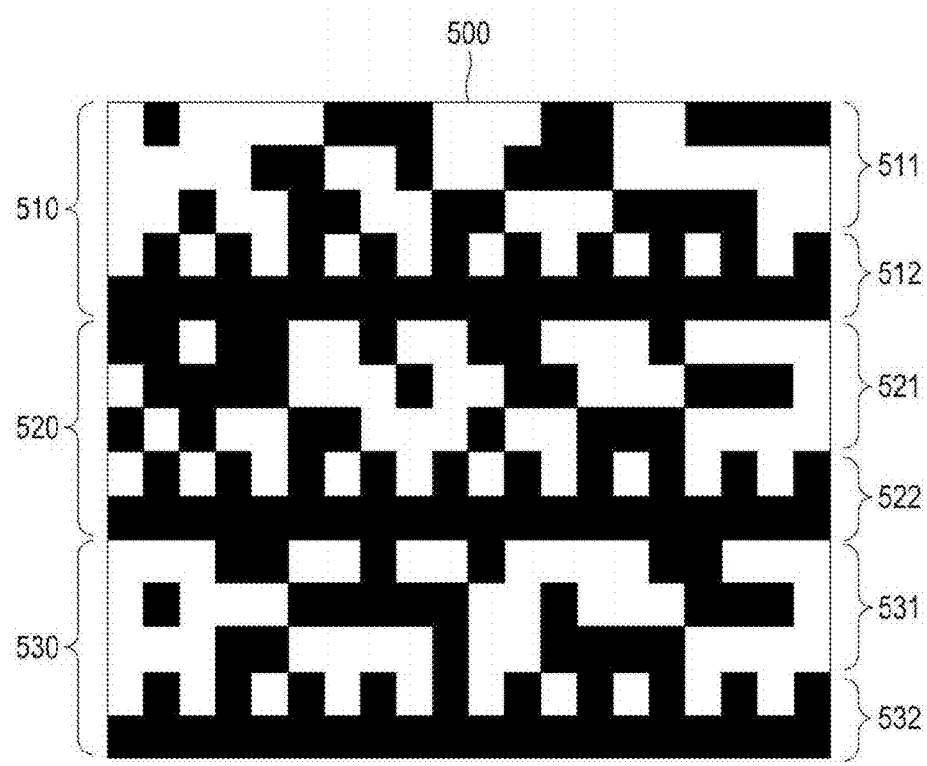
FIG. 5 is a diagram of a pattern, according to one embodiment of the present disclosure, according to one embodiment of the present.

FIG. 5 shows a pattern 500, according to one embodiment of the present disclosure. In one embodiment, the pattern 500 may be formed by arranging one or more horizontal patterns (e.g., horizontal patterns 510, 520, and 530) in a column direction. In this embodiment, it is assumed that the pattern 500 is formed by arranging three horizontal patterns 510, 520, and 530 in the column direction in the present embodiment. As shown, the horizontal patterns 510, 520, and 530 may include sequence groups 511, 521, and 531, respectively, which include a plurality of rows of binary-coded sequences, respectively. According to one embodiment, each of the binary-coded sequences included in the sequence groups 511, 521, and 531 may include aperiodic sequences that are repeatedly arranged.

Here, the "aperiodic sequences that are repeatedly arranged" may indicate that the respective aperiodic sequences internally have a maximized auto-correlativity (the same sub-sequence is not shown two times or more in a single aperiodic sequence) and a deterministic randomness (the unique location of each sub-sequence is predetermined in a single aperiodic sequence), whereas there is a minimized cross-correlativity (different aperiodic sequences can be surely distinguished from each other) between the aperiodic sequences and such aperiodic sequences may be repeated two times or more in a single binary-coded sequence.

According to one embodiment, each aperiodic sequence may include a plurality of sub-sequences arranged in a predetermined order. For example, each aperiodic sequence may be a Pseudo-Random Binary Sequence (PRBS), and more specifically, may be a De Bruijn Sequence. In this case, the "aperiodic sequence," as described above, may mean that it has a maximized auto-correlativity or a plurality of sub-sequences included in the corresponding sequence is not arranged in a periodic manner. The configuration of such an aperiodic sequence will be described in more detail below.

According to one embodiment, the horizontal patterns 510, 520, and 530 may include meta-sequence groups 512, 522, and 532 that can separate adjacent sequence groups from each other among the sequence groups 511, 521, and 531. Each of the meta-sequence groups 512, 522, and 532 may include one or more meta-sequences.

The meta-sequence may be distinguished from the binary-coded sequence included in the sequence groups. If the sequence groups 511, 521, and 531 are formed such that adjacent sequence groups are separated from each other in the pattern 500, the meta-sequence groups 512, 522, and 532 may be omitted in the pattern 500.

According to one embodiment, the meta-sequence may be a periodic sequence that has a minimized auto-correlativity (one sub-sequence is repeated in the meta-sequence) and a maximized cross-correlativity.

According to another embodiment, the meta-sequence may be an aperiodic sequence that is not used in the sequence groups.

Although FIG. 5 illustrates that the meta-sequence is disposed to separate the sequence groups from each other in the horizontal direction, the meta-sequence may be disposed to separate the sequence groups from each other in a vertical direction, according to one embodiment. In another embodiment, the meta-sequence may be disposed to separate the sequence groups from each other in horizontal and vertical directions.

Figure 6:
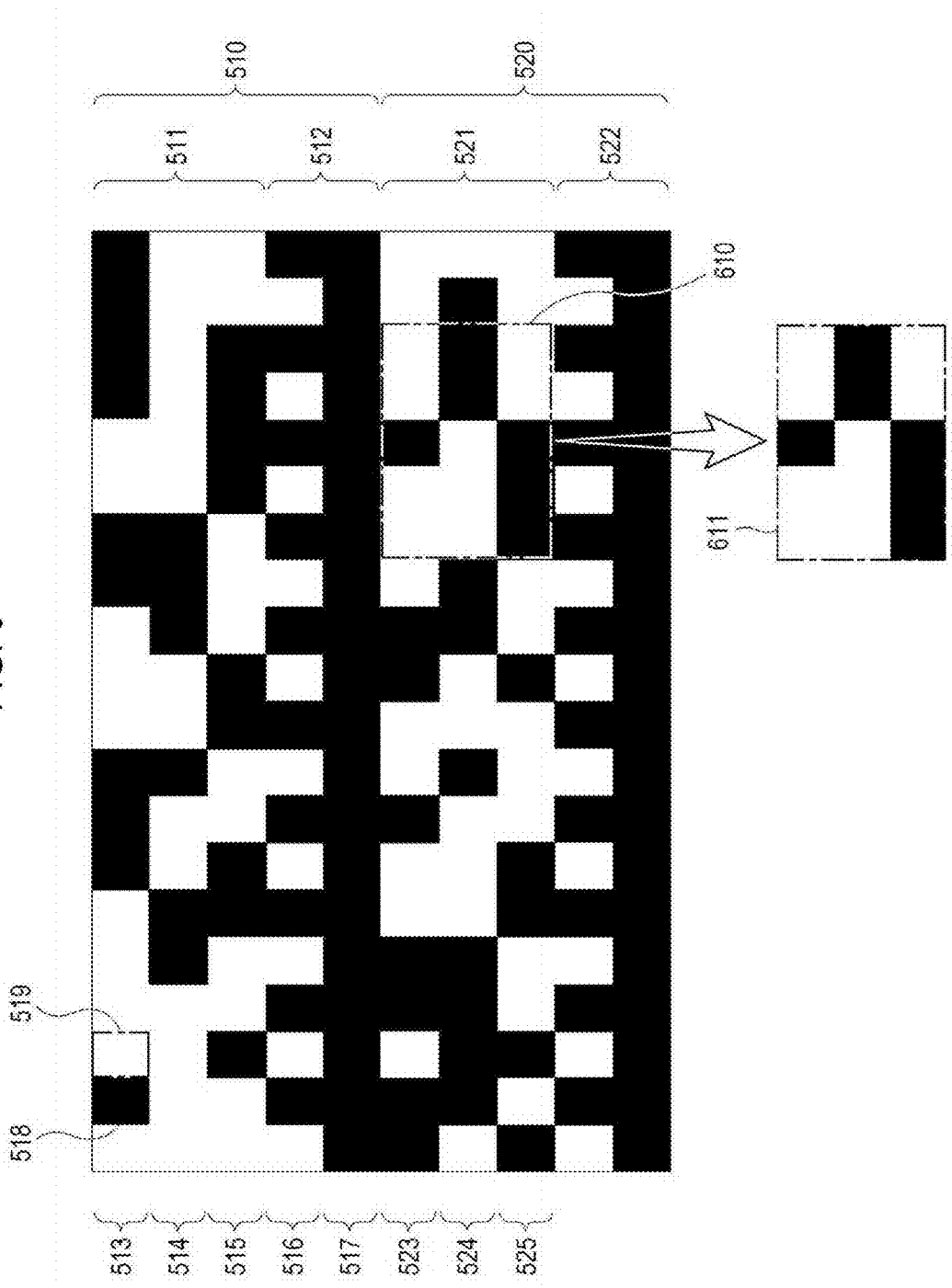
FIG. 6 depicts a diagram that explains a pattern, according to one embodiment of the present disclosure.

FIG. 6 is a diagram that shows a detailed configuration of two adjacent horizontal patterns 510 and 520 in the pattern 500. According to one embodiment, each of the horizontal patterns 510 and 520 may include sequence groups 511 and 521, respectively, and each of the sequence groups 511 and 521 includes a plurality of rows of binary-coded sequences. In the present disclosure, the horizontal pattern 510 includes the sequence group 511 that includes three binary-coded sequences 513, 514, and 515, and the horizontal pattern 520 includes the sequence group 521 that includes three binary-coded sequences 523, 524, and 525. The binary-coded sequences 513, 514, and 515 may be arranged to be sequentially adjacent in a column direction, and the other binary-coded sequences 523, 524, and 525 may also be arranged to be sequentially adjacent in a column direction.

Each of the binary-coded sequences 513, 514, and 515 may include aperiodic sequences that are repeatedly arranged. According to one embodiment, the aperiodic sequences (or sub-sequences) that are included in one of the binary-coded sequences 513, 514, and 515 may be different from the aperiodic sequences (or sub-sequences) that are included in another of the binary-coded sequences. For example, the number of bits of each of the sub-sequences included in the binary-coded sequence 513 may be different from the number of bits of each of the sub-sequences included in the binary-coded sequence 514.

According to one embodiment, the horizontal pattern 510 may include a meta-sequence group 512 configured to separate the sequence group 511 included in the horizontal pattern 510 from the sequence group 521 included in another horizontal pattern 520. The meta-sequence group 512 may include one or more meta-sequences, and the meta-sequence may be easily distinguished from the binary-coded sequences included in the sequence groups 511 and 521.

According to one embodiment, the meta-sequence group 512 may include at least one of a meta-sequence 516 formed of different binary codes that are alternately repeated or a meta-sequence 517 formed of the same binary code that is repeated. In this case, the meta-sequence 516 may be a reference to separate between bit patterns (for example, a bit pattern 518 and a bit pattern 519) that represent binary codes constituting the binary-coded sequences 513, 514, and 515. In addition, the meta-sequence 517 may be a reference that is able to separate between the sequence groups 511 and 521.

Here, if the filled bit pattern 518 may correspond to a binary code "1," a blank bit pattern 519 may correspond to a binary code "0," or vice versa.

According to one embodiment, each of the sequence groups 511 and 521 may be created by splitting a single long sequence group. Therefore, the binary-coded sequences located in the same row in the respective sequence groups 511 and 521 may be sequences in which the same aperiodic sequence is repeatedly arranged. For example, the binary-coded sequence 513 of the sequence group 511 and the binary-coded sequence 523 of the sequence group 521 may be sequences in which the same aperiodic sequence is repeatedly arranged, and the binary-coded sequence 514 of the sequence group 511 and the binary-coded sequence 524 of the sequence group 521 may be sequences in which the same aperiodic sequence is repeatedly arranged.

If the sequence group 511 includes two binary-coded sequences 513 and 514; another sequence group 521 includes two binary-coded sequences 523 and 524; and if the horizontal pattern 510 does not include the meta-sequence group 512, the binary-coded sequence 513 and the binary-coded sequence 523 may be arranged to be spaced two rows apart in a column direction. This is similar to the situation in which the meta-sequence group 512 is configured with two rows that includes only blank bit patterns. Likewise, the binary-coded sequence 514 and the binary-coded sequence 524 may also be arranged to be spaced two rows apart in the column direction. Therefore, the binary-coded sequences located in the same row in the adjacent sequence groups may be arranged to be spaced at least two rows apart in the column direction. If the number of binary-coded sequences included in each sequence group increases or the meta-sequence group is included in the horizontal pattern, the binary-coded sequences located in the same row in the adjacent sequence groups may be arranged to be spaced three or more rows apart.

According to one embodiment, the binary-coded sequence 513 may include binary codes that are different from each other, and the binary codes may be implemented in any shapes that are easily distinguished in the naked eye, such as the bit pattern 518 and the bit pattern 519. The different binary codes may be the bit patterns 518 and 519 in a rectangular shape as shown in FIG. 6, or may be implemented as a bit pattern in various forms including one of a circle, a rhombus, a triangle, a pentagon, etc.

According to some embodiments, when the capturing unit 330 of the optical tracking system 300 captures an image of at least a part of the pattern 500 formed on the marker 310, the processor 350 may determine the posture of the marker 310 based on the location of each sub-pattern (for example, some of the binary-coded sequences included in the sequence group), which is included in the pattern 500, in the entire pattern 500. For example, if the captured pattern image includes the pattern 500 as shown in FIG. 6, the processor 350 may identify the sub-pattern through a sequence window 610 in the sequence group 521. The size of the sequence window 610 may be equal to, or greater than, the size of the sub-pattern.

The sub-pattern may be formed of a sequence block 611 that includes the sub-sequences of the respective binary-coded sequences 523, 524, and 525. The processor 350 may use the sub-sequences included in the sequence block 611, and determine the location of the corresponding sub-pattern (or the sequence block 611) in the entire pattern 500, and may determine the posture of the marker 310 based on the determined location of the sub-pattern. According to one embodiment, the "sequence block" may have a size of j×l, where j may be the number of a plurality of rows of binary-coded sequences (or parts thereof) included in the sequence block, and l may be the number of bits of the longest sub-sequence among the sub-sequences included in the sequence block.

According to one embodiment, each of the binary-coded sequences included in the pattern 500 may include aperiodic sequences that are repeatedly arranged, such as the PRBS, and the order (or the locations) of the sub-sequences in the respective aperiodic sequences may be predetermined. For example, the processor 350 may extract the sequence block corresponding to the sub-pattern from the image of the captured pattern 500, and may extract the sub-sequences, or some of them, constituting the PRBS in the sequence block in order to determine the location of the sub-pattern in the entire pattern 500 based on the location information of the extracted sub-sequence.

In some embodiments, the PRBSs having a length of 2n bits, which is to be included in a pattern, may be created by using a shift register of n bits that has modulo-2 feedback. Each of sub-sequences of n bits in each of the PRBSs created as described above may be arranged in a predetermined location in the PRBS. According to another embodiment, the PRBSs may be created by performing a repeated XOR-operation for an input value and an output value of the shift register of n bits. According to some other embodiments, the PRBSs may be created by using the Fibonacci linear feedback shift register. However the method of creating the binary-coded sequences that are included in the pattern used in the present disclosure is not limited to the PRBS creation method described above, and, for example, well-known methods, such as QRSS (Quasi-random Sequence signal), or various binary-coded sequence creation methods similar to the same may be applied to the present disclosure.

According to another embodiment, the pattern 500 may be formed by using the De Bruijn Sequence that is a kind of the PRBS. The De Bruijn Sequence may be generally expressed in the form of B(k,n). Here, k denotes the size of a circuit sequence of predetermined alphabets, and n denotes an order that may refer to the length (the number of bits) of each of the sub-sequences constituting the De Bruijn Sequence. All the sub-sequences constituting the De Bruijn Sequence have the same length (the same number of bits), but have different bit arrays from each other. That is, each of the sub-sequences to form the De Bruijn Sequence may have a unique bit array in the De Bruijn Sequence, and thus each sub-sequence may appear only once in the De Bruijn Sequence. According to such a characteristic, the De Bruijn Sequence may be an aperiodic sequence in which the sub-sequences included therein are not periodically arranged. In addition, the order or location of each of the sub-sequences in the De Bruijn Sequence may be predetermined.

Figure 7:
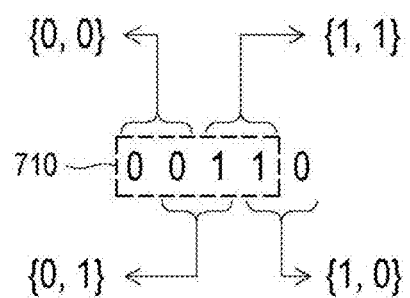
FIG. 7 illustrates a diagram of a configuration of a De Bruijn Sequence.

FIG. 7 is a diagram of a configuration of the De Bruijn Sequence in which a De Bruijn Sequence 710 is expressed as B(2,2) as an example. The De Bruijn Sequence 710 of B(2,2) may be expressed as {0, 0, 1, 1}. In one embodiment, the De Bruijn Sequence 710 of B(2,2) may include, as basic alphabets, binary codes "0" and "1" having a size of 2, and may be formed by sequentially arranging {0, 0}, {0, 1}, {1, 1}, and {1, 0}, which are different sub-sequences having a length of 2.

As described above, the De Bruijn Sequence has a characteristic in which the order of each of the sub-sequences constituting the same is predetermined according to a value of an attribute variable (k, n). In the case of the De Bruijn Sequence 710 of B(2,2), {0, 0} is the first, {0, 1} is the second, {1, 1} is the third, and {1, 0} is the fourth in the sequence {0, 0, 1, 1}. Therefore, based on the respective values (or bit arrays) of the sub-sequences that are arranged in the De Bruijn Sequence, it may be determined where the sub-sequence is located in the De Bruijn Sequence 710.

According to the configuration and characteristics of the De Bruijn Sequence described above, aperiodic sequences having a length of $2^n$ bits may be created by using the De Bruijn Sequence of n-th order, such as B(2, n). Therefore, when any sub-sequence having a length of n bits is obtained from the aperiodic sequences as formed above, the location of the corresponding sub-sequence may be determined in the De Bruijn Sequence based on a value of the corresponding sub-sequence. When a pattern of the marker 310 is formed by using such a De Bruijn Sequence, based on the sub-sequence having a length of n bits that has been extracted from the captured pattern image, the location of the sub-pattern including the sub-sequence may be determined in the entire pattern.

Figure 8:
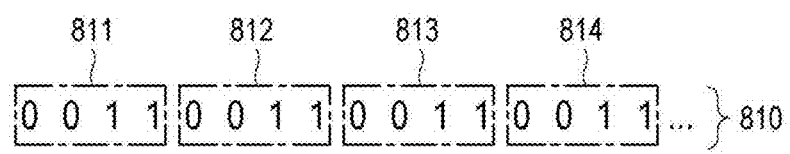
FIG. 8 is a diagram that shows a binary-coded sequence in which a De Bruijn Sequence is repeated.

Meanwhile, as shown in FIG. 8, in the case of the binary-coded sequence 810 in which the same De Bruijn Sequence 811, 812, 813, or 814 is repeatedly arranged, each of the De Bruijn Sequences 811, 812, 813, and 814 that are repeatedly arranged includes sub-sequences of the same array. Therefore, it is difficult to determine where the corresponding sub-sequence is positioned in the De Bruijn Sequences based on the value of a sub-sequence that is extracted from such De Bruijn Sequences 811, 812, 813, and 814. In this case, the location of the corresponding sub-sequence may be determined in the binary-coded sequence 810 only if the location of the De Bruijn Sequence including the corresponding sub-sequence is determined first in the binary-coded sequence 810.

Meanwhile, the binary-coded sequence that is used to form a pattern has an enough length to form the pattern. The length of the binary-coded sequence may increase as the order n of the binary-coded sequence increases regardless of whether the binary-coded sequence is the De Bruijn Sequence or PRBS. In addition, as the order n of the binary-coded sequence increases, the length of each sub-sequence included in the sequence increases as well. For example, the De Bruijn Sequence of the 21st order may have a length of $2^{21}$=2,097,152 bits, but the length of each sub-sequence included in the sequence is 21 bits. Therefore, when the longer De Bruijn Sequence is required to form a pattern, the order of the sequence becomes more than 21, and the length of the sub-sequence included in the sequence becomes more than 21 bits.

Figure 9:
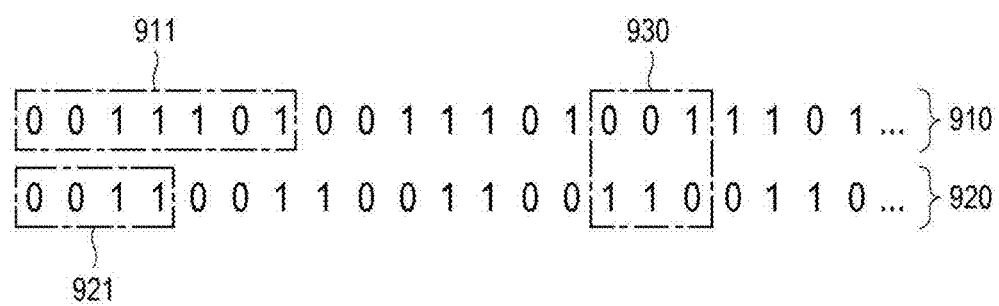
FIG. 9 describes a diagram that explains a method of implementing a pattern that is formed on the marker by using a De Bruijn Sequence of B(2,3)-1 and a De Bruijn Sequence of (2,2), according to one embodiment of the present disclosure.

According to one embodiment, in the case of creating a sequence for forming a pattern by using a plurality of De Bruijn Sequences of which the orders are different from each other, a sequence that is long enough to form the pattern may even be created by using the De Bruijn Sequence of relatively low order. FIG. 9 shows an diagram in which a De Bruijn Sequence 911 of B(2,3)-1 and a De Bruijn Sequence 921 of B(2,2) are used together in order to form a pattern, according to one embodiment. The De Bruijn Sequence 911 of B(2,3)-1 is a modified De Bruijn Sequence that is created by using the remaining sub-sequences except for the sub-sequence {0, 0, 0} that includes only "0" among the sub-sequences constituting the De Bruijn Sequence of B(2,3). In the case of the De Bruijn Sequence 911 {0, 0, 1, 1, 1, 0, 1} of B(2,3)-1, seven sub-sequences {0, 0, 1}, {0, 1, 1}, {1, 1, 1}, {1, 1, 0}, {1, 0, 1}, {0, 1, 0}, and {1, 0, 0} may be arranged in predetermined locations in the sequence 911. Meanwhile, the De Bruijn Sequence 921 of B(2,2) has the same configuration as the De Bruijn Sequence 710 that has been described with reference to the FIG. 7. The reason why the pattern is created by using a normal De Bruijn Sequence together with a modified De Bruijn Sequence instead of only by using normal De Bruijn Sequences will be described in more detail below.

The De Bruijn Sequence 911 of B(2,3)-1 may have a length of $2^3-1=7$ bits, and sub-sequences of the sequence 911 may have a length of 3 bits, respectively. Thus, when considering only the De Bruijn Sequence 911 of B(2,3)-1, the total length of the binary-coded sequence required for obtaining the location information of the sub-sequence is 7 bits, and the sub-sequence may have a length of 3 bits. In addition, the De Bruijn Sequence 921 of B(2,2) may have a length of $2^2=4$ bits, and the sub-sequence having the location information may have a length of 2 bits.

When binary-coded sequences 910 and 920 in which two De Bruijn Sequences 911 and 921 that have the configuration described above are repeatedly arranged, respectively, are combined in the column direction, a pattern including two rows may be formed. In this pattern, the binary-coded sequences 910 and 920 of two rows may be repeated in a cycle of 7×4=28 bits corresponding to the least common multiple of the lengths of the De Bruijn Sequences 911 and 921. In this case, {0, 0, 1, 1, 1, 0, 1} that is the De Bruijn Sequence 911 of B(2,3)-1 may be repeated four times, and {0, 0, 1, 1} that is the De Bruijn Sequence 921 of B(2,2) may be repeated seven times in the binary-coded sequences 910 and 920 of two rows that have a cycle of 28 bits. Therefore, when the De Bruijn Sequences of two rows are combined to then form a pattern, the length in which the pattern has an aperiodic characteristic may be greater than the length in which the combined De Bruijn Sequences 911 and 921 have an aperiodic characteristic.

In the binary-coded sequences 910 and 920 that are combined as described above, a sequence window 930 may be placed in a certain location of the binary-coded sequences 910 and 920, which has a size of 2×3, wherein the number of columns corresponds to the number of bits (i.e., 3) of the longest sub-sequence among the sub-sequences of two De Bruijn Sequences 911 and 921 and the number of rows corresponds to the number of combined sequences (i.e., 2) so that a sequence block may be extracted through the sequence window 930. The location of the sequence block in the binary-coded sequences 910 and 920 may be determined by using the sub-sequences {0, 0, 1} and {1, 1} that are in the leftmost location in the sequence block.

In the present disclosure, the size of a pattern region that is to be captured by the capturing unit 330 for the tracking of the marker 310 may be determined according to the number of bits of the columns and rows of the sequence window. For example, in the embodiment of FIG. 9, the sequence block may be extracted from the captured pattern region through the sequence window 930 in a size of 2×3, and the location of the extracted sequence block may be determined in the sequences 910 and 920 having a length of 28 bits.

On the contrary, likewise, a sequence (or pattern) having a length of 28 bits may be created by using the De Bruijn Sequence of the fifth order {for example, a single B(2,5)}, but, in this case, the length of the sub-sequence included in the pattern becomes 5 bits.

Therefore, compared with the case where a pattern is created by using a single De Bruijn Sequence of the same length, in the case where a pattern is created by using the combined De Bruijn Sequences 910 and 920 of the same length as shown in the embodiment of the present disclosure, the size of the sequence window for identifying the sub-sequence included in the sequence block may be significantly reduced.

This means that the conditions for the size of a region that is required for the capturing unit 330 to accurately capture an image for tracking the marker 310 may be relaxed and the possibility in which the processor 350 successfully identifies every moment the sub-sequence from the captured region in the pattern image may be considerably improved.

For example, in the embodiment of FIG. 9, if bit patterns of 3 bits in the horizontal and 2 bits in the vertical are accurately identified in at least one portion of the captured pattern image, the location of the sequence block including sub-sequences corresponding to the corresponding bit patterns may be determined in the pattern. On the contrary, in the case of using the De Bruijn Sequence of the fifth order, only if the bit patterns of 5 bits in the horizontal are accurately identified in at least one portion of the captured pattern image, the location of the sequence block including sub-sequences corresponding to the corresponding bit patterns may be determined in the pattern.

In order to determine a more precise location, for example, when using a pattern of the combined De Bruijn Sequences B(2,7)-1, B(2,6), B(2,5)-1, B(2,4)-1, and B(2,3)-1, if only bit patterns of 7 bits in the horizontal (the length of the sub-sequence) and 5 bits in the vertical (the number of the De Bruijn Sequences) {when considering meta-sequences, bit patterns of 7 bits in the horizontal and 7 bits in the vertical (a sum of the number of the De Bruijn Sequences and the number of meta-sequences)} are accurately identified in at least one portion of the captured pattern image, the location of the sequence block including sub-sequences corresponding to the corresponding bit patterns may be determined in the pattern. On the contrary, in the case of using the De Bruijn Sequence of the 25th order of the same length, only if all bit patterns of 25 bits in the horizontal are accurately identified in at least one portion of the captured pattern image, the location of the sub-sequence corresponding to the corresponding bit patterns may be determined in the pattern.

Meanwhile, the captured image may have a distortion caused by a relative moving speed, rotating, and tilting of the marker and the capturing unit, a distortion cause by the characteristics of the optical system, a distortion caused by thermal noise, vibration, and read-out properties of the image sensor, or the like. Thus, as the length of the sequence window increases in one direction, the possibility in which all the bit patterns that are extracted through the sequence window are accurately identified may decrease. In the example above, the sequence window of 7 bits in the horizontal and 5 bits in the vertical is almost always more advantageous than a sequence window of 25 bits in the horizontal and 1 bit in the vertical.

Meanwhile, as shown in the embodiment described with reference to FIG. 9, some of the De Bruijn Sequences constituting the combined binary-coded sequences may be the modified De Bruijn Sequences, except for the sub-sequence that includes only "0." It is due to the fact that the repetition cycle of the combined binary-coded sequences becomes a least common multiple of the lengths (the number of bits) of the De Bruijn Sequences. Therefore, if the least common multiple of the lengths of the De Bruijn Sequences is increased by: (i) increasing the number of binary-coded sequences to be combined to form a pattern; (ii) setting the orders of the De Bruijn Sequences constituting the binary-coded sequence to be different from each other; or (iii) properly excluding the sub-sequence that includes only "0" from the De Bruijn Sequences constituting the binary-coded sequence, the longer combined binary-coded sequences may be created. As described above, the number of the De Bruijn Sequences to be combined to form a pattern, the order of each De Bruijn Sequence, and the exclusion of the sub-sequence that includes only "0" from the De Bruijn Sequences may be appropriately selected according to the length of the combined binary-coded sequence, which is required to form the pattern.

For example, it is assumed that a pattern is formed by using five De Bruijn Sequences and the De Bruijn Sequences are B(2,7)-1, B(2,6), B(2,5)-1, B(2,4)-1, and B(2,3)-1. As a result, the total length of the combined binary-coded sequence that has an aperiodic characteristic may be $(2^7-1) \times (2^6) \times (2^5-1) \times (2^4-1) \times (2^3-1) = 26{,}456{,}640$ bits. This length may be obtained only if the De Bruijn Sequence of at least the 25th order is used. If the sub-sequence that includes only "0" is not excluded from the De Bruijn Sequence of B(2,5), the total length of the aperiodic sequence may decrease to $(2^7-1) \times (2^5) \times (2^4-1) \times (2^3-1) = 426{,}720$ bits. This is merely a length of pattern that can be obtained by using the De Bruijn Sequence of the 19th order.

Figure 10:
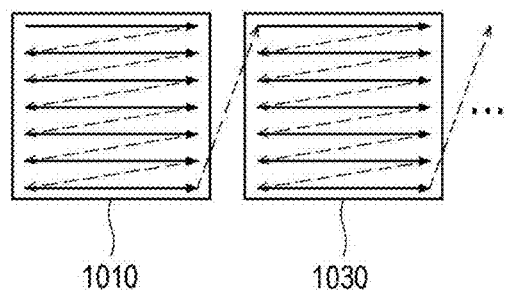
FIG. 10 depicts a diagram showing a method for implementing a two-dimensional pattern by using a single long horizontal pattern that is formed according to one embodiment of the present disclosure.

FIG. 10 depicts a diagram showing a method for implementing a two-dimensional pattern by using a single long horizontal pattern that is formed by combining a plurality of rows of binary-coded sequences, according to one embodiment of the present disclosure. According to one embodiment, a single long horizontal pattern may be divided into several patterns having a smaller length, and then, the divided patterns may be arranged in a plurality of rows in order to thereby implement a two-dimensional pattern 1010. According to another embodiment, a single long horizontal pattern may be divided into several patterns having a smaller length, and then, the divided patterns may be arranged in a plurality of rows in order to thereby implement another two-dimensional pattern 1030. Thereafter, a new two-dimensional pattern may be implemented by sequentially combining the two-dimensional patterns 1010 and 1030.

According to one embodiment, when dividing a single horizontal pattern to then create a two-dimensional pattern, the whole or a part of the horizontal pattern may be used. For example, a horizontal pattern of 1,000 bits long may be divided into 10 patterns having a length of 100 bits, and then, the 10 patterns may be arranged in a plurality of rows so that a two-dimensional pattern may be implemented. As another example, the two-dimensional pattern may also be implemented by dividing only 800 bits of the horizontal pattern of 1000 bits long. In addition, 10 markers that have different patterns from each other may be made by dividing the horizontal pattern of 1000 bits long into 10 horizontal patterns of 100 bits long and forming the 10 divided horizontal patterns (or sequence) on the 10 markers, respectively.

According to one embodiment, when a plurality of patterns are made, which are to be used for a plurality of markers, by dividing a single horizontal pattern as described above, the sequence block itself that is extracted from each of the divided patterns through a sequence window may be used as the ID of the corresponding marker. For example, a horizontal pattern is assumed, which has 1,000 sequence blocks that are identified through a sequence window. When the horizontal pattern is divided into 10 small patterns that include 100 sequence blocks and the 10 divided small patterns are used as the patterns for 10 markers, respectively, the marker may be predetermined so that the pattern includes 1,000 sequence blocks among the 10 markers. For example, the first marker may be predetermined to include the first to 100th sequence blocks, and the second marker may be predetermined to include the 101st to 200th sequence blocks. Likewise, the sequence blocks to be included in the remaining third to tenth markers may be predetermined.

Therefore, based on such information, the processor 350 may determine an ID of the marker that is currently tracked only by determining the location information of the sequence block that is extracted for tracking among the 1,000 sequence blocks. In the example above, if the processor 350 determines that the extracted sequence block corresponds to the 120th sequence block, the processor 350 may recognize that the marker corresponds to the second marker. That is, even if the pattern of the marker does not include a separate pattern or code information to provide the ID of the marker, the processor 350 may distinguish the corresponding marker from other markers based on the location information of the sequence block, which is extracted from the pattern of the marker.

With regard to the marker 310, according to one embodiment of the present disclosure, as described above, the pattern information may be identified through the optical system 312, such as lenses, from the outside of the marker 310 by installing a light source inside or outside the marker 310 and by allowing the light from the light source to be reflected by, or pass through, the pattern plane 311 on which a pattern is formed. The pattern plane 311 on which a pattern is formed may be implemented by using a material having a high or low reflectivity for the light in order to reflect or transmit the light from the light source. Here, the "reflectivity" may refer to a ratio of the energy of the light incident on the pattern plane to the energy of the light that is reflected by the pattern plane.

According to one embodiment, in the case of implementing the pattern by using the binary-coded sequences, the portions where different binary codes, such as "0" or "1," are implemented on the pattern plane may be formed of materials having different reflectivities for the light, respectively. When the pattern implemented on the pattern plane, which is formed as described above, is captured by the capturing unit 330, the amount of the light transferred to the capturing unit 330 varies with "0" or "1" constituting the pattern so that "0" and "1" may be separately identified in the pattern image. According to another embodiment, the portions that represent "0" or "1" in the pattern may be formed in different images or shapes. For example, an image representing "0" in the pattern may be expressed as a circle, and an image representing "1" may be expressed as a rectangle. However, the method for expressing the binary-coded sequences or the binary codes included in the sequences on the pattern is not limited thereto, and they may be implemented in other various images or shapes.

According to one embodiment, the marker 310 may include an optical system 312, such as lenses, to allow at least a part of the pattern to be visually identified from the outside of the marker 310. The pattern plane 311 may be disposed inside the marker 310 in order for the pattern to be transferred to the outside of the marker 310 in the form of a parallel outgoing light through the optical system 312. In the case where the pattern plane 311 is disposed inside the marker 310 as described above, the optical system of the marker 310 may be combined with the optical system of the capturing unit 330 of the optical tracking system 300 in order to thereby configure an infinite optical system. The capturing unit 330 of the optical tracking system 300 may obtain a pattern image of the pattern, which is enlarged through the infinite optical system. Therefore, in the case of the infinite optical system that is configured as described above, even if the marker 310 is located far away from the capturing unit 330, at least a part of the pattern can be identified from the pattern image that is captured by the capturing unit 330.

According to one embodiment, in order for the pattern to be transferred to the outside of the marker 310 in the form of a parallel outgoing light, the pattern may be implemented in a portion of the pattern plane 311 where the focal point of the lens constituting the optical system 312 is formed. According to one embodiment, the pattern plane 311 on which a pattern is formed may have a flat or curved surface. In this case, the lens constituting the optical system 312 may be designed such that the focal point of the lens may be formed on the flat or curved surface of the pattern plane 311. For example, if the optical system 312 is designed by using a fisheye lens, the focal point of the lens may be formed on the flat or curved surface of the pattern plane 311.

<Capturing Unit>

As described with reference to FIG. 3 above, in order to capture an image of a pattern for tracking the marker 310, the capturing unit 330 may include two or more capturing elements 332 and 334, and lenses 331 and 333 corresponding to the same. At least a part of the pattern, which can be identified from the outside of the marker 310, may be captured by the capturing elements 332 and 334 through the lens 331 and the lens 333.

In the capturing unit 330, according to one embodiment of the present disclosure, the capturing elements 332 and 334 may be installed to be fixed in the focal lengths of the lenses 331 and 333 corresponding to the capturing elements 332 and 334, respectively. As a result, the capturing elements 332 and 334 may be positioned at the afocal point that is the focal point of the optical system that is configured by combining the optical system 312 of the marker 310 and the lenses 331 and 333 of the capturing unit 330, respectively. In this case, the capturing elements 332 and 334 may capture an enlarged image for the whole or a part of the pattern that is formed on the marker 310 regardless of a change in distance from the marker depending on the movement of the marker 310. In addition, the capturing unit 330 may capture an image of the pattern without focusing, even if the marker 310 is moved.

In one embodiment, the capturing elements 332 and 334 may be disposed to have a proper angle or direction in the capturing unit 330 in order to obtain a pattern image for the same region of a pattern that is formed on the marker 310.

Likewise, in the case where the optical tracking system 400 includes two capturing units 430 and 440 as shown in FIG. 4, the capturing elements 432 and 442 that are included in the capturing units 430 and 440, respectively, may be installed to be fixed in the focal lengths of the corresponding lenses 431 and 441. In addition, the capturing elements 430 and 440 may be disposed to have a proper angle or direction in the optical tracking system 400 in order to obtain a pattern image for the same region of a pattern that is formed on the marker 310.

Meanwhile, when at least a part of the pattern is captured as a pattern image by the capturing element in the outside of the marker 310, the size of the region where at least a part of the pattern is captured on the pattern image may vary with at least one of the distances from the location (for example, the location of the capturing unit), where the pattern image is captured, to the marker 310 and the location of the marker 310, respectively.

<Processor>

The optical tracking system 300, according to one embodiment of the present disclosure, may include a processor 350 that is able to calculate the location and the posture of the marker 310 based on the information that is extracted from at least a part of the pattern included in the pattern image that is obtained by the capturing unit 330.

Figures 11, 12:
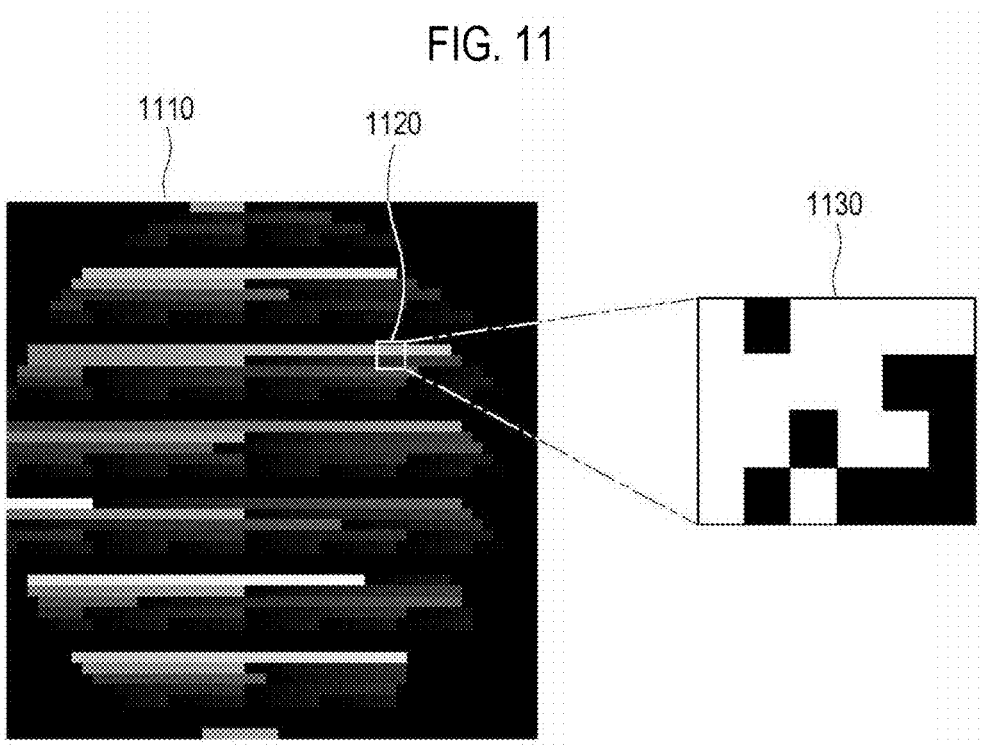
FIG. 11 illustrates a diagram that explains a method for determining the posture and ID of a marker based on a pattern image of the marker, which is captured in a capturing unit of the optical tracking system, according to one embodiment of the invention.
FIG. 12 is a flowchart of a method for tracking a marker in an optical tracking system, according to one embodiment of the present disclosure.

In some embodiments, the processor 350 may extract the size of the pattern region and the central coordinates of the pattern region from the captured pattern image, and may determine the location of the marker 310 based on the same. For example, in the case where the shape and aperture of the optical system that are formed by the marker 310 and the capturing unit 330 are circles, the pattern region in the pattern image may be shown in an approximately circular shape or in a part of the circular shape as shown in FIG. 11. The size of the circular shape representing the pattern region on the pattern image may vary with the distance from the capturing unit 330 to the marker 310 or with the location of the marker 310. The processor 350 may extract the diameter and central coordinates of a circle that represents the pattern region on the pattern image, and may compare the same with the diameter and focal length of the lens corresponding to the capturing element of the capturing unit 330 in order to thereby obtain coordinate values corresponding to the location of the marker 310 in the three-dimensional space with a central point of the lens as the origin. In this case, when a plurality of lenses is implemented to correspond to the capturing element, the plurality of lenses may be defined as a single thin lens according to the well-known thin lens theory. Accordingly, the diameter, the focal length, and the central point of the lens corresponding to the capturing element of the capturing unit 330 may be expressed as the diameter, the focal length, and the central point of a single thin lens, respectively, which is defined as described above.

According to another embodiment, the processor may determine the location of the marker 310 by using triangulation. The processors 350 and 450 may extract the central coordinates of the pattern regions (for example, the central coordinates of the circular shape in FIG. 11) from the pattern images that are captured by the capturing elements 332 and 334 or the capturing units 430 and 440 that are placed in different locations, and may calculate the location of the marker 310 by using triangulation based on the central coordinates. For example, the processor 350 and 450 may calculate the location of the marker 310 by using the central coordinates of the pattern region on each pattern image and by using a geometric relationship between the directions in which the capturing elements 332 and 334 or the capturing units 430 and 440 view the marker 310. In this case, the capturing elements 332 and 334 or the capturing unit 430 and 440 are placed in different locations.

According to another embodiment, the processor 350 may determine the locations of two markers by using pattern images for the two markers that have a predetermined geometric relationship. For example, when the capturing unit captures pattern images of patterns that are formed on two markers, the processor 350 may determine the locations of the two markers based on a geometric relationship between the two markers and based on a relationship between the location of at least a part of the pattern on the pattern image and the location of at least a part of the pattern on each marker. In this case, the distance between the patterns that are formed on the two markers may be determined from the geometric relationship between the two markers. The processor 350 may determine the locations of the two markers based on the location relationship above by using the central coordinates of the pattern on each marker.

A method for determining the location of the marker 310 by the processor 350 may be conducted by properly selecting one of the well-known algorithms, and one example thereof is disclosed in Korean Patent No. 10-1406220.

According to one embodiment, the processor 350 may determine the posture of the marker 310 based on a location change of at least a part (for example, the sub-pattern) of the pattern on the pattern image. The processor 350 may obtain a posture matrix R that represents the posture of the marker 310 by using Equation 1 based on such a principle.

$$s \begin{bmatrix} u'_i \\ v'_i \\ 1 \end{bmatrix} = [A][R][C] \begin{bmatrix} u_i \\ v_i \\ 1 \end{bmatrix} = \begin{bmatrix} -\frac{f_c}{pw.} & 0 & u'_c \\ 0 & -\frac{f_c}{ph.} & v'_c \\ 0 & 0 & 1 \end{bmatrix} \begin{bmatrix} r_{11} & r_{12} & r_{13} \\ r_{21} & r_{22} & r_{23} \\ r_{31} & r_{32} & r_{33} \end{bmatrix} \begin{bmatrix} 1 & 0 & -u_c \\ 0 & 1 & -v_c \\ 0 & 0 & f_b \end{bmatrix} \begin{bmatrix} u_i \\ v_i \\ 1 \end{bmatrix}$$

[Equation 1]

In Equation 1, $s = r_{31}u_i + r_{32}v_i + r_{33}f_b$; $u'_i$, $v'_i$ denotes the pixel coordinates of the i-th sub-pattern on the pattern image; $u_i$, $v_i$ denotes the coordinates of the i-th sub-pattern on the pattern; $u_c$, $v_c$ denotes the actual coordinates of the central point of the pattern; pw denotes a pixel area of the pattern image; ph denotes a pixel height of the pattern image; $f_c$ denotes a focal length of the lens corresponding to the capturing element; and $f_b$ denotes a focal length of the lens of the marker.

In order to execute a calculation according to Equation 1, the processor 350 may extract the location of each sub-pattern (for example, the coordinates of the i-th sub-pattern on the pattern in Equation 1) in the pattern from the pattern image. The pattern, according to one embodiment of the present disclosure, may be formed by using the binary-coded sequences that are formed by the De Bruijn Sequences that are repeatedly arranged. The processor 350 may extract, through a sequence window, one or more sequence blocks constituting the sub-patterns from the pattern image including the whole or a part of the pattern that is formed as described above, and may determine the location (coordinates) of the sequence block on the pattern by using the sub-sequences included in the sequence block.

Hereinafter, a method in which the processor 350 determines the location of each sub-pattern from the pattern image of the pattern that is formed by using the De Bruijn Sequences will be described in detail.

First, in order to extract the information for tracking the marker from the pattern image, the processor 350 may read binary-coded sequences from the pattern image. Next, the processor 350 may extract one or more sequence blocks constituting the sub-pattern from the read binary-coded sequences, and may calculate the location (coordinates) of each sub-pattern in the whole pattern by using the sub-sequences included in each sequence block.

According to one embodiment, the processor 350, as shown in FIG. 11, may: i) extract a single sequence block 1130 through the sequence window 1120 from the pattern 1110 that is formed by using the De Bruijn Sequences; and ii) obtain the location of the sub-pattern that includes one sequence block 1130 based on the sub-sequences included in the same. For example, a simultaneous equation for obtaining the location information of one sequence block 1130 may be derived by using a characteristic in which the sub-sequences imply the location information on the De Bruijn Sequence and by using a characteristic in which all the lengths between the start bits of the binary-coded sequences and the start bit of the sequence block 1130 are the same in the binary-coded sequences. The processor 350, based on the values of the simultaneous equation, may calculate the location of the sub-pattern including a single sequence block 1130 in the whole pattern, and may determine the posture of the marker 310 based on the same.

The processor 350 may calculate the posture of the marker 310 based on only a single sequence block as described above. If a plurality of sequence blocks is extracted, the processor 350 may calculate a plurality of postures of the marker 310 by using all or some of the plurality of sequence blocks extracted from the pattern image, and may determine the posture of the marker 310 through a statistical operation of the calculation result. In this case, the statistical operation may refer to an operation for obtaining an average, a median value, or a mode value, but it is not limited thereto.

<Method for Tracking Marker>

FIG. 12 is a flowchart of a method for tracking a marker on which a pattern is formed in an optical tracking system, according to one embodiment of the invention. Hereinafter, a method for tracking the marker 310 will be described in more detail in relation to each operation with reference to the drawing.

First, in operation S1210, one or more capturing elements that are included in one or more capturing units may obtain a pattern image for at least a part of a pattern. For example, referring to FIG. 4, the capturing elements 432 and 442 included in the capturing units 430 and 440, respectively, may capture the pattern image for at least a part of the pattern, which can be visually identified from the outside of the marker 310 through the optical system 312, based on the focal lengths of the lenses 431 and 441 corresponding to the capturing elements 432 and 442, respectively. In this case, if the pattern is implemented on the pattern plane 311 on which the focal point of the optical system 312 is formed, the optical tracking system 400 may form an infinite optical system. The capturing units 430 and 440 may capture an enlarged image of at least a part of the pattern, as the pattern image, through the infinite optical system, respectively.

The pattern, according to one embodiment of the present disclosure, may include a plurality of rows of binary-coded sequences. The binary-coded sequence of each row may include aperiodic sequences that are repeatedly arranged, such as a De Bruijn Sequence. In this case, each of the aperiodic sequences constituting a plurality of rows of binary-coded sequences may include a plurality of sub-sequences that are arranged in a predetermined order.

According to one embodiment, the aperiodic sequences that are included in one of the plurality of rows of binary-coded sequences may be different from the aperiodic sequences that are included in another of the plurality of rows of binary-coded sequences. For example, the number of bits in each sub-sequence included in the binary-coded sequence in one row may be different from the number of bits in each sub-sequence included in the binary-coded sequence in another row. The number of bits of the sub-sequence in the De Bruijn Sequence may be determined according to the order of the De Bruijn Sequence. The detailed configuration of the pattern of the embodiments above has been described before, which will be omitted here.

When the pattern image is obtained through operation S1210, the processor may process the information that is extracted from at least a part of the pattern that is included in the pattern image in order to thereby track the location and the posture of the marker in operation S1220. For example, referring to FIG. 4, the processor 450 may process the information extracted from at least a part of the pattern that is included in the pattern image that is obtained by the capturing elements 432 and 442 in order to thereby track the location and the posture of the marker 310.

In one embodiment, the method for tracking the location and the posture of the marker 310, which is executed in operation S1220, will be described in detail with reference to FIG. 13. First, in operation S1221, the processor may determine the location of the marker based on triangulation by using pattern images obtained by two or more capturing units or two or more capturing elements. For example, referring to FIG. 3, the processor 350 may determine the location of the marker 310 by using triangulation based on the pattern images that are obtained by the capturing elements 332 and 334 that are placed in different locations. In addition, referring to FIG. 4, the processor 450 may determine the location of the marker 310 by using triangulation based on the pattern images that are obtained by the capturing units 430 and 440 that are placed in different locations.

According to one embodiment, the processors 350 and 450 may determine the location of the marker 310 based on triangulation by using the central coordinates of the pattern region (for example, the central coordinates of a circle in FIG. 11) on each pattern image and a geometric relationship between the directions in which the capturing units 430 and 440 or the capturing elements 332 and 334 view the marker 310. Although the location of the marker is determined by using triangulation in the embodiments above, it is not limited thereto, and other location determining methods rather than triangulation may be used. In this case, operation S1221 may be omitted.

In operation S1222, the processor may extract one or more sequence blocks from the pattern images. For example, referring to FIGS. 3 and 6, the processor 350 may extract, through the sequence window 610 having a predetermined size, at least one sequence block 611 from the pattern image that is obtained by the capturing unit 330. The sequence block 611 may include some of a plurality of rows of binary-coded sequences constituting the pattern.

According to one embodiment, the sequence block may include a sub-sequence that corresponds to each of the plurality of rows of binary-coded sequences. The sequence block may have a size of j×1, wherein j may be the number of binary-coded sequences that are included in the sequence block, and 1 may be the number of bits of the longest sub-sequence among the sub-sequences included in the sequence block.

When one or more sequence blocks are extracted as described above, in operation S1223, the processor may determine the posture of the marker based on the one or more extracted sequence blocks. In some embodiments, first, the processor may determine the location of the sub-pattern in the pattern, which is represented by the sequence block, based on the sub-sequences included in each of a plurality of rows of binary-coded sequences that are included in the sequence block. Thereafter, the processor may determine the posture of the marker based on the determined location of the sub-pattern in the pattern. For example, referring to FIGS. 5 and 6, the processor 350 may determine the location of the sub-pattern in the whole pattern 500, which is formed by the sequence block 611, by using the sub-sequences that are included in the extracted sequence block 611. The processor 350 may determine the posture of the marker 310 based on the determined location of the sub-pattern in the whole pattern 500.

In the embodiment described with reference to FIG. 13, the processor determines the posture of the marker 310 after determining the location of the marker. In another embodiment, the processor may determine the posture of the marker prior to determining the location of the marker. In some embodiments, the processor may determine the location and the posture of the marker by processing the same in parallel.

Although the method has been described through specific embodiments, the method may also be embodied as computer-readable codes in a computer-readable recording medium. The computer-readable recording medium includes all kinds of recording devices that store data that can be read by a computer system. The examples of the computer-readable recording medium may include ROM, RAM, CD-ROM, magnetic tapes, floppy disks, optical data storage devices, or the like, or may be implemented in the form of a carrier wave (for example, the transmission through the Internet). In addition, the computer-readable recording medium may be distributed to computer systems that are connected through a network, and a computer-readable code may be stored and executed in a distributed manner. In addition, functional programs, codes, and code segments for implementing the embodiments above may be easily inferred by the programmers who are skilled in the art.

Although the present disclosure has been described in relation to some embodiments in the present specification, it should be noted that there may be various modifications and changes without departing from the spirit and scope of the present disclosure, which can be understood by those skilled in the art. In addition, such modifications and changes should be construed to belong to the scope of the claims appended herein.

What is claimed is:

1. A marker with a pattern formed thereon, comprising: an optical system, wherein:
   at least a part of the pattern that uniquely appears depending on a direction in which the pattern is viewed from an outside of the marker through the optical system, is visually identified from the outside of the marker;
   the pattern includes a plurality of rows of binary-coded sequences;
   the binary-coded sequence of each of the plurality of rows includes aperiodic sequences that are repeatedly arranged;
   the aperiodic sequences included in the binary-coded sequence of one row of the plurality of rows are different from the aperiodic sequences included in the binary-coded sequence of another row of the plurality of rows; and
   each of the aperiodic sequences includes a plurality of sub-sequences that are arranged in a predetermined order.

2. The marker according to claim 1, wherein the plurality of rows of binary-coded sequences include a first binary-coded sequence and a second binary-coded sequence that are adjacent in a column direction, and
   wherein a number of bits of each of the sub-sequences included in the first binary-coded sequence is different from a number of bits of each of the sub-sequences included in the second binary-coded sequence.

3. The marker according to claim 2, wherein the pattern further include a third binary-coded sequence positioned in a m-th row from the first binary-coded sequence in the column direction and a fourth binary-coded sequence positioned in the m-th row from the second binary-coded sequence in the column direction,
   wherein the aperiodic sequence included in the third binary-coded sequence is equal to the aperiodic sequence included in the first binary-coded sequence, and the aperiodic sequence included in the fourth binary-coded sequence is equal to the aperiodic sequence included in the second binary-coded sequence, and
   wherein m is a natural number of 2 or more.

4. The marker according to claim 3, wherein the pattern includes:
   a first sequence group including the first and second binary-coded sequences;
   a second sequence group including the third and fourth binary-coded sequences; and
   a meta-sequence configured to separate the first and second sequence groups from each other.

5. The marker according to claim 4, wherein the meta-sequence is different from the binary-coded sequences that are included in the first and second sequence groups.

6. The marker according to claim 5, wherein the meta-sequence is a sequence in which different binary codes are alternately repeated, or is comprised of only the same binary code.

7. The marker according to claim 1, further comprising a pattern plane on which the pattern is formed,
   wherein different binary codes that are included in the binary-coded sequences of the pattern formed on the pattern plane are made of materials that have different reflectivities from each other.

8. The marker according to claim 1, further comprising a pattern plane on which the pattern is formed,
   wherein the optical system includes a lens, and the pattern is formed in a portion where a focal point of the lens is formed on the pattern plane.

9. The marker according to claim 8, wherein the pattern plane has a flat or curved surface, and the lens allows the focal point to be formed on the flat or curved surface.

10. The marker according to claim 1, wherein the aperiodic sequence is a PRBS (Pseudo-Random Binary Sequence) or De Bruijn Sequence.

11. The marker according to claim 1, wherein if at least a part of the pattern is captured as a pattern image in the outside of the marker, a size of a region where at least a part of the pattern is captured on the pattern image varies with at least one of a distance from a location in which the pattern image is captured to the marker or a location of the marker.

12. An optical tracking system comprising:
one or more markers on which a pattern is formed;
one or more capturing units configured to include one or more capturing elements that obtains a pattern image of the pattern; and
a processor configured to track locations and postures of the one or more markers based on information that is extracted from at least a part of the pattern included in the pattern image, wherein:
the pattern includes a plurality of rows of binary-coded sequences; the binary-coded sequence of each of the plurality of rows includes aperiodic sequences that are repeatedly arranged; the aperiodic sequences included in the binary-coded sequence of one row of the plurality of rows are different from the aperiodic sequences included in the binary-coded sequence of another row of the plurality of rows; and each of the aperiodic sequences includes a plurality of sub-sequences that are arranged in a predetermined order.

13. The optical tracking system according to claim 12, wherein the optical tracking system extracts one or more sequence blocks from the pattern image and then tracks the one or more markers, and wherein the one or more sequence blocks include a part of the plurality of rows of binary-coded sequences.

14. The optical tracking system according to claim 13, wherein the one or more sequence blocks have a size of j×1 in which j denotes a number of binary-coded sequences that are included in the one or more sequence blocks and 1 denotes a number of bits of a longest sub-sequence among the plurality of sub-sequences included in the one or more sequence blocks.

15. The optical tracking system according to claim 13, wherein the processor determines postures or IDs of the one or more markers based on the one or more sequence blocks.

16. The optical tracking system according to claim 15, wherein the part of the plurality of rows of binary-coded sequences are sub-sequences that are included in each of the plurality of rows of binary-coded sequences, and
wherein the processor determines a location of a sub-pattern represented by the one or more sequence blocks in the pattern based on the sub-sequences, and determines the postures of the one or more markers based on the location of the sub-pattern.

17. The optical tracking system according to claim 15, wherein the part of the plurality of rows of binary-coded sequences are sub-sequences that are included in each of the plurality of rows of binary-coded sequences, and
wherein the processor determines location information on the one or more sequence blocks in the plurality of binary-coded sequences based on the sub-sequences, and determines the IDs of the one or more markers based on the location information.

18. The optical tracking system according to claim 12, wherein the one or more capturing units include two or more capturing units, or the one or more capturing elements include two or more capturing elements, and
wherein the processor determines the locations of the one or more markers based on triangulation by using pattern images that are obtained by the two or more capturing units or by the two or more capturing elements.

19. The optical tracking system according to claim 18, wherein the processor determines the locations of the one or more markers based on central coordinates of a region of the pattern on each of the pattern images and triangulation by using a geometric relationship between directions in which the two or more capturing units or the two or more capturing elements view the one or more markers.

20. The optical tracking system according to claim 12, wherein the processor determines the locations of the one or more markers based on a size of a region of the pattern and central coordinates of the pattern region, on the pattern image obtained by the one or more capturing units.

21. The optical tracking system according to claim 12, wherein the one or more markers include two markers that has a predetermined geometric relationship,
wherein the capturing units capture pattern images of patterns that are formed on the two markers, respectively, and
wherein the processor determines the locations of the two markers based on the predetermined geometric relationship and a relationship between a location of at least a part of the patterns on the pattern images and a location of at least a part of the pattern on each of the markers.

22. The optical tracking system according to claim 12, wherein the plurality of rows of binary-coded sequences include a first binary-coded sequence and a second binary-coded sequence that are adjacent in a column direction, and
wherein a number of bits of each sub-sequence included in the first binary-coded sequence is different from a number of bits of each sub-sequence included in the second binary-coded sequence.

23. The optical tracking system according to claim 22, wherein the pattern further includes a third binary-coded sequence positioned in a m-th row from the first binary-coded sequence in the column direction and a fourth binary-coded sequence positioned in the m-th row from the second binary-coded sequence in the column direction,
wherein the aperiodic sequence included in the third binary-coded sequence is equal to the aperiodic sequence included in the first binary-coded sequence, and the aperiodic sequence included in the fourth binary-coded sequence is equal to the aperiodic sequence included in the second binary-coded sequence, and
wherein m is a natural number of 2 or more.

24. The optical tracking system according to claim 12, wherein the one or more markers include a first lens,
wherein the pattern is implemented on a pattern plane on which a focal point of the first lens is formed, and
wherein the one or more capturing units include a second lens that is configured such that at least a part of the pattern, which is visually identified from the one or more markers in a direction in which the capturing units view the one or more markers through the first lens, is captured on the one or more capturing elements, and obtains a pattern image of at least a part of the pattern in a focal length of the second lens.

25. The optical tracking system according to claim 24, further comprising a light source configured to emit light onto the one or more markers in order to enhance the light incident on the second lens through the first lens with respect to at least a part of the pattern.

26. An optical tracking method for tracking a marker on which a pattern is formed, the method comprising:
obtaining, by one or more capturing elements included in one or more capturing units, a pattern image of at least a part of the pattern; and
proceeding, by a processor, information extracted from at least a part of the pattern included in the pattern image and tracking a location and a posture of the marker, wherein:
the pattern includes a plurality of rows of binary-coded sequences; the binary-coded sequence of each of the plurality of rows includes aperiodic sequences that are repeatedly arranged; the aperiodic sequences included in the binary-coded sequence of one row of the plurality of rows are different from the aperiodic sequences included in the binary-coded sequence of another row of the plurality of rows; and each of the aperiodic sequences includes a plurality of sub-sequences that are arranged in a predetermined order.

27. The method according to claim 26, wherein the tracking the location and the posture of the marker comprises extracting one or more sequence blocks from the pattern image, and wherein the one or more sequence blocks have a size of j×1 in which j denotes a number of binary-coded sequences that are included in the one or more sequence blocks and 1 denotes a number of bits of a longest sub-sequence among the sub-sequences included in the one or more sequence blocks.

28. The method according to claim 27, wherein the tracking the location and the posture of the marker comprises determining the posture of the marker based on the one or more extracted sequence blocks.

29. The method according to claim 28, wherein the determining the posture of the marker comprises:
determining a location of a sub-pattern represented by the one or more sequence blocks in the pattern based on the sub-sequences that are included in each of the plurality of rows of binary-coded sequences that are included in the one or more sequence blocks; and
determining the posture of the marker based on the determined location of the sub-pattern.

30. The method according to claim 26, wherein the one or more capturing units include two or more capturing units, or the one or more capturing elements include two or more capturing elements, and
wherein the tracking the location and the posture of the marker comprises determining the location of the marker based on triangulation by using pattern images that are obtained by the two or more capturing units or by the two or more capturing elements.

31. The method according to claim 30, wherein the determining the location of the marker based on the triangulation comprises determining the location of the marker based on central coordinates of the pattern region on each of the pattern images and triangulation by using a geometric relationship between directions in which the two or more capturing units or the two or more capturing elements view the marker.

32. A computer-readable recording medium that stores a program that includes instructions for executing operations of the optical tracking method according to claim 26.

* * * * *